United States Patent [19]

McEwen

[11] Patent Number: 4,479,494

[45] Date of Patent: Oct. 30, 1984

[54] ADAPTIVE PNEUMATIC TOURNIQUET

[75] Inventor: James A. McEwen, Richmond, Canada

[73] Assignee: Western Clinical Engineering Ltd., Richmond, Canada

[21] Appl. No.: 337,152

[22] Filed: Jan. 5, 1982

[51] Int. Cl.³ .............................................. A61B 17/12
[52] U.S. Cl. ..................................... 128/327; 128/682
[58] Field of Search ................ 128/682, 327, 686, 691

[56] References Cited

U.S. PATENT DOCUMENTS 4,321,929  3/1982  Lemelson et al. .................. 128/630

FOREIGN PATENT DOCUMENTS 1253501  11/1971  United Kingdom ................ 128/682

OTHER PUBLICATIONS

"Complications Of and Improvements In Pneumatic Tourniquets Used in Surgery", J. A. McEwen, *Medical Instrumentation*, 15:4, Jul.-Aug. 1981.

Primary Examiner—Michael H. Thaler

Attorney, Agent, or Firm—Klarquist, Sparkman, Campbell, Leigh & Whinston

[57] ABSTRACT

A pneumatic tourniquet for maintaining occluded or restricted blood flow into a patient's limb includes an inflatable cuff, a pressurizing mechanism for pressurizing the cuff, a pressure relief mechanism for depressurizing the cuff, a blook pressure sensing mechanism for sensing the patient's systolic blood pressure and for producing a blood pressure output signal representative thereof, and a pressure regulator mechanism responsive to the blood pressure output signal for selectably activating the pressurizing mechanism and the pressure relief mechanism to maintain a substantially constant pressure difference between the cuff pressure and the patient's systolic blood pressure.

Thus, the cuff pressure may be varied "adaptively" in response to changes in the patient's intra-operative systolic blood pressure to pressurize the cuff close to the minimum level required to maintain a bloodless surgical field, thereby minimizing the risk of patient injury due to over-pressurization of the cuff.

17 Claims, 16 Drawing Figures

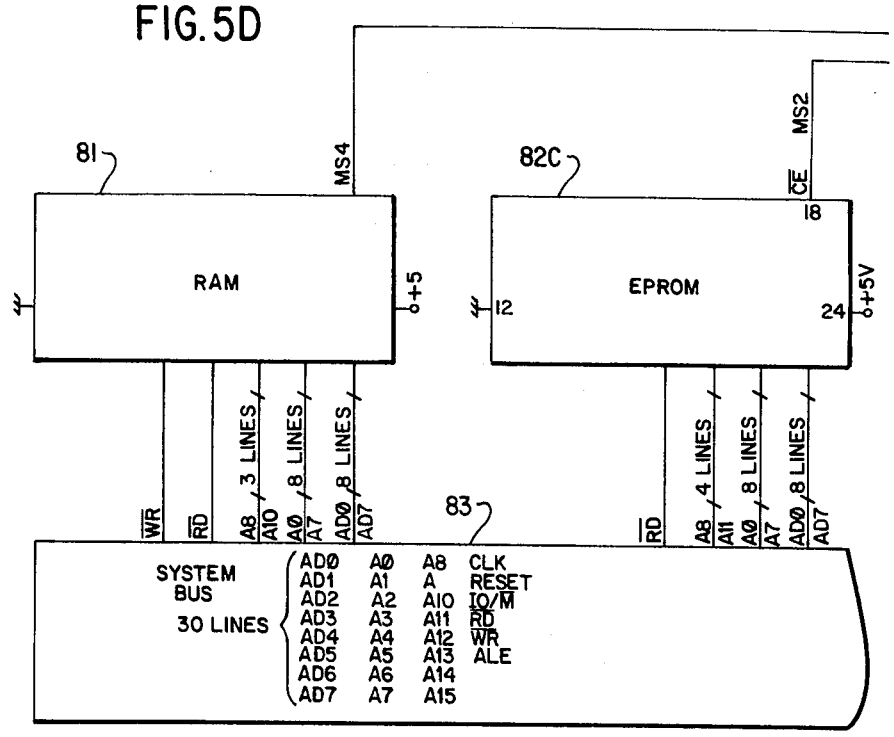

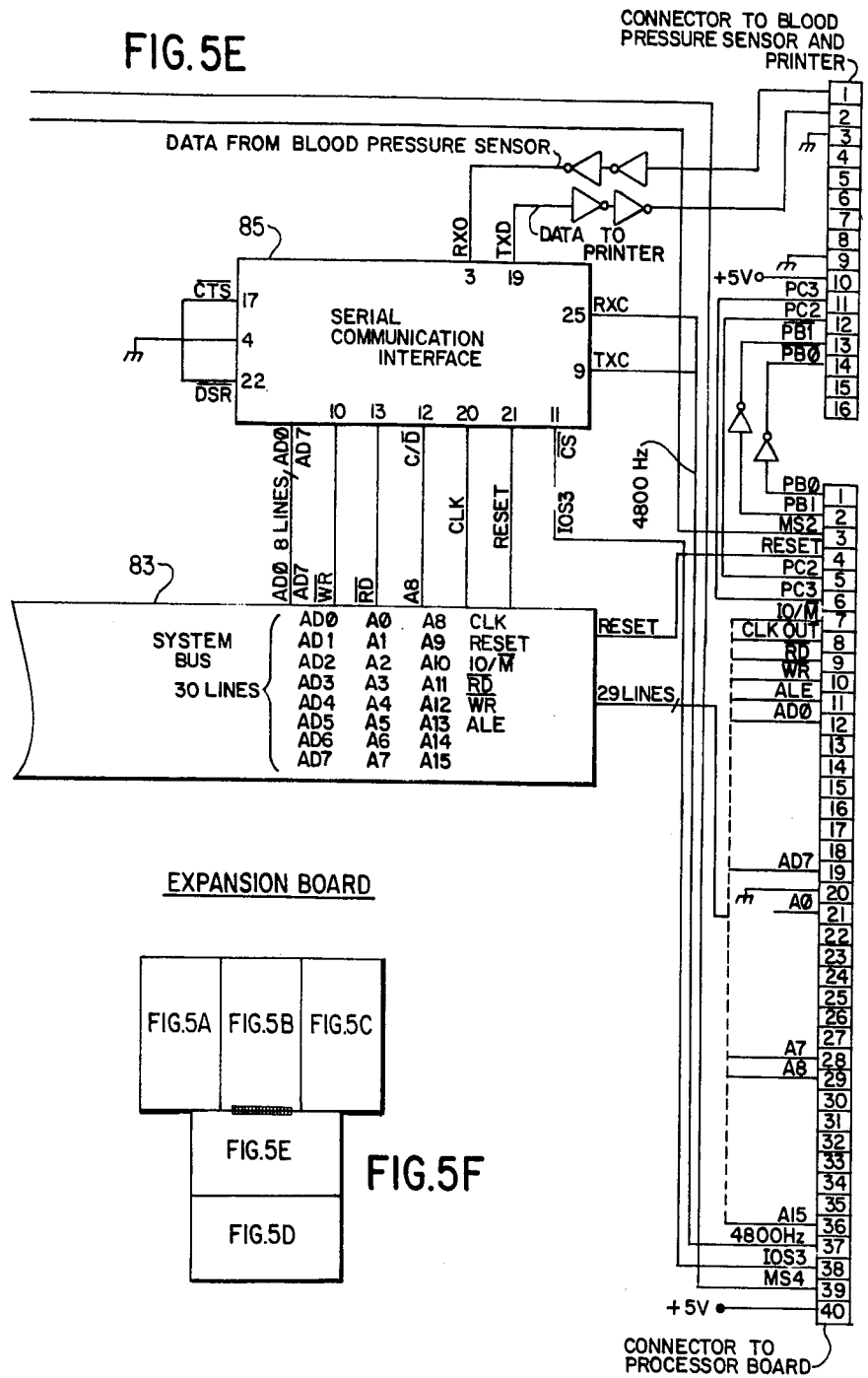

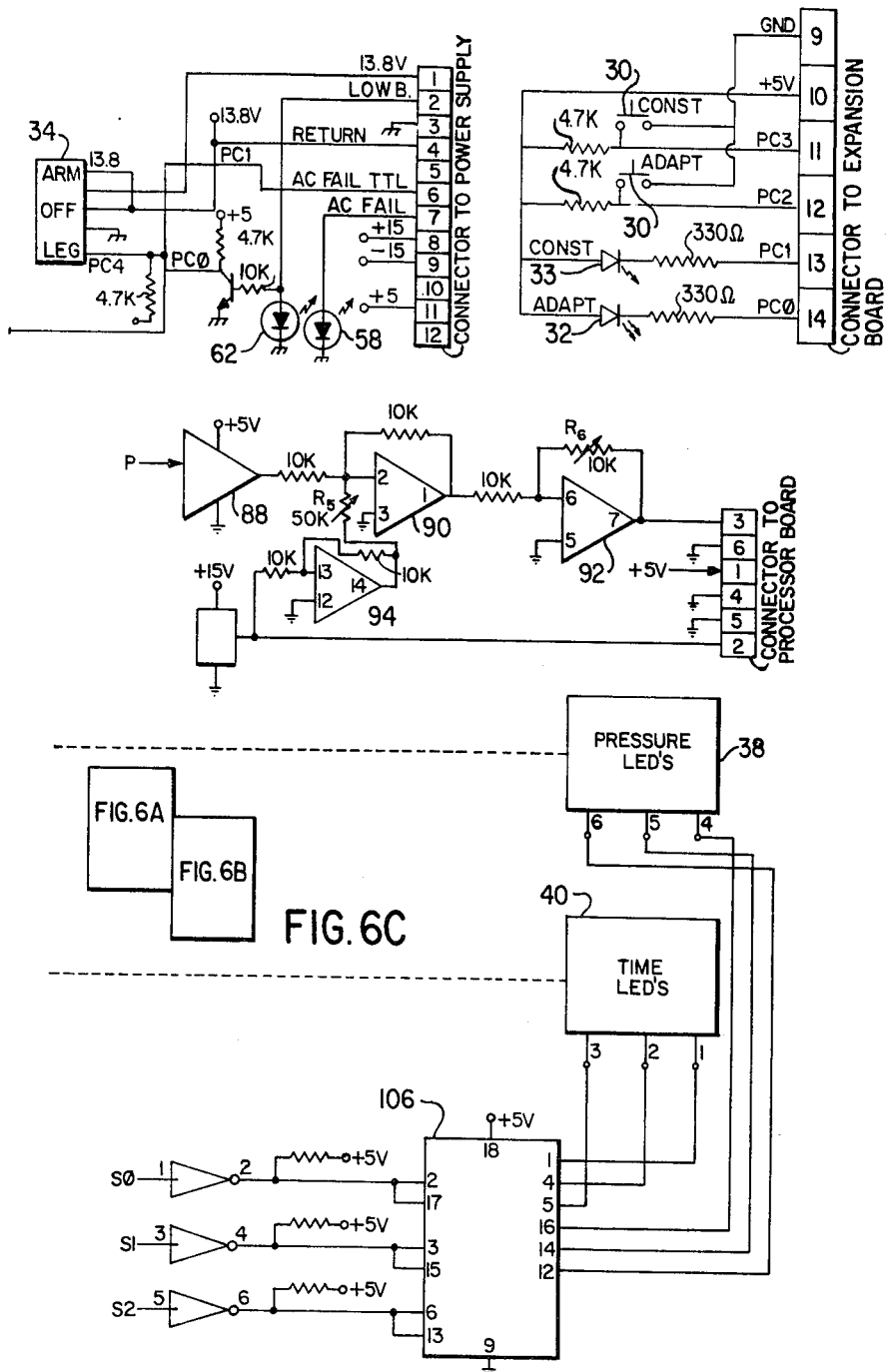

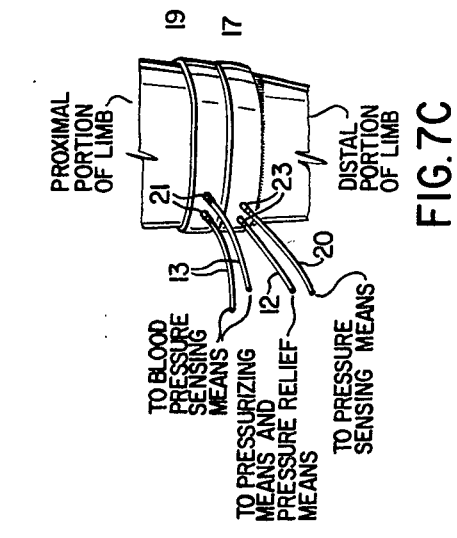
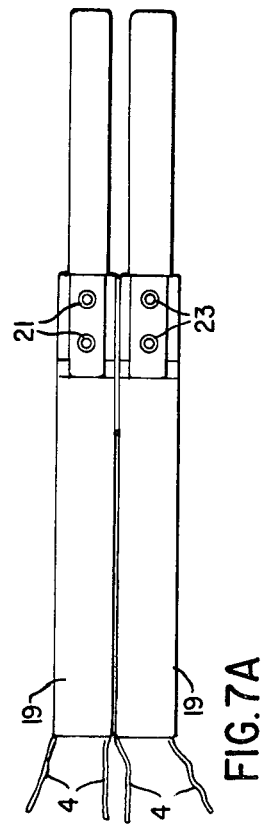
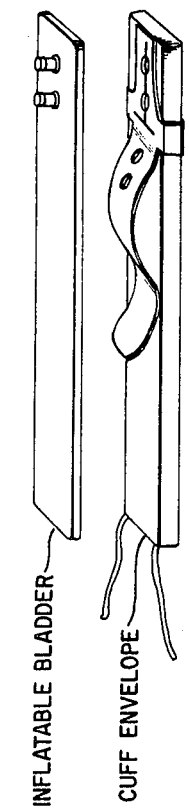

ADAPTIVE PNEUMATIC TOURNIQUET

FIELD OF THE INVENTION

This invention pertains to pneumatic tourniquets for maintaining occluded or restricted blood flow into a patient's limb while surgical procedures are performed on the limb. In particular, the invention pertains to pneumatic tourniquets having means for automatically sensing and controlling the pressure in an inflatable cuff which encircles the limb.

BACKGROUND OF THE INVENTION

Conventional pneumatic tourniquets typically provide an inflatable cuff which may be wrapped around a proximal portion of a patient's limb, a source of compressed gas for inflating the cuff, a pressure gauge for measuring the cuff pressure, and a pressure regulating mechanism. Typically, the cuff is wrapped around the patient's limb and inflated with compressed gas to a supra-systolic pressure as high as 650 millimetres of mercury ("mmHg") in order to stop the flow of blood into the distal portion of the limb. A surgeon is thus provided with a "bloodless field" in which surgical procedures may be performed on the limb. Maintaining a bloodless surgical field makes dissection easier, renders surgical procedures less traumatic, and generally shortens the time required to complete the surgical procedure. The pressure gauge provides the operator with an indication of cuff pressure. The pressure regulating mechanism in such conventional devices is intended to maintain the cuff pressure relatively constant.

It has been estimated that about 10,000 conventional pneumatic tourniquets are currently used in about 1,000,000 surgical procedures performed annually in North America. Regrettably, the widespread use of pneumatic (and non-pneumatic) tourniquets in surgery has been accompanied by continuing reports of limb paralysis, nerve damage and other injuries believed to be attributable to tourniquets. A survey of the literature indicates that such complications may result from many factors, including:

1. Excessive cuff pressure (which may lead to nerve compression and other damage at the cuff site).
2. Insufficient cuff pressure (which may lead to passive congestion or hemorrhagic infiltration of the nerve).
3. Excessive periods of application of an inflated tourniquet to the limb.
4. Application of the tourniquet cuff without consideration of the local limb anatomy.

Many reported cases of preventable nerve damage, limb paralysis and other injuries are believed to have resulted from the factors listed above, the most common of which appears to be overpressurization of the cuff [see, for example: D. K. Wheeler and P. R. Lipscomb, A Safety Device for a Pneumatic Tourniquet, *J. Bone Joint Surg.*, 45A:870, 1964; W. K. Hamilton and M. D. Sokoll, Tourniquet Paralysis, *Journal of the American Medical Association*, 199:37, 1967; S. J. Prevoznik, Injury from Use of Pneumatic Tourniquets, *Anesthesiology*, 32:177, 1970; J. M. Bruner, Time, Pressure and Temperature Factors in the Safe Use of the Tourniquet, *Hand*, 2:39-42, 1970; D. Fry, Inaccurate Tourniquet Gauges, *Br. Med. J.*, 1:511, 1972; A. E. Flatt, Tourniquet Time in Hand Surgery, *Arch. Surg.*, 104:190-192, 1972; G. Burchell and G. Stack, Exsanguination of the Arm and Hand, *Hand*, 5:124-126, 1973]. Unfortunately, the actual incidence of tourniquet-induced complications in surgery may not be reliably estimated because the "tourniquet paralysis syndrome" (to borrow a phrase from J. Moldaver, Tourniquet Paralysis Syndrome, *Arch, Surg.* 68:136-144, 1954) may be difficult to detect or may be masked by the effects of surgery, because the damage is generally transient and reversible to a large extent and because such incidents may not be consistently reported due to concern over potential legal liability. (A hospital was recently found liable for nerve injuries suffered by a patient as a result of excessive pressure applied to her arm by a tourniquet ["Hospital Liable to Patient for Tourniquet Paralysis", *Citation*, 38:5, Oct. 15, 1978]).

Conventional tourniquets examined by the inventor which have been linked to possible nerve injuries or paralysis associated with cuff over-pressurization have been found to have malfunctioning pressure regulating mechanisms or inherent hysteresis in the pressure regulating mechanism which permitted the cuff pressure to rise about 150-400 mmHg above the desired cuff pressure (which is typically in the 200-650 mmHg range). Similar findings have been made by other investigators [see, for example: D. L. Johnson, P. D. Neufeld and R. G. Hussey, Hazards in Single-Stage Regulation of Pressure Cuffs; *J. Clin. Eng.*, Vol. 5, pp. 59-62, 1980.] Other tourniquets have been found to have aneroid pressure gauges which produced readings inaccurate by about 200 mmHg.

Ideally, a pneumatic tourniquet should be inflated to the minimum supra-systolic pressure required to maintain a bloodless surgical field distal to the cuff. Simultaneous maintenance of a bloodless surgical field and minimization of tourniquet cuff pressure should help to minimize the likelihood of pressure related injuries [see: R. Sanders, the Tourniquet: Instrument or Weapon?, *Hand*, 5:119-123, 1973; and, J. C. Adams, *Standard Orthopaedic Operations*, Churchill P. Livingston, New York, 1976, pp. 4-5].

Theoretically, the minimum cuff pressure required to maintain a bloodless surgical field distal to the cuff should be equal to or slightly greater than the patient's systolic blood pressure, which is the maximum blood pressure produced during each cycle of the heart. However, a patient's systolic blood pressure may continually change (particularly when surgical procedures are being performed on the patient). Thus, one practical approach would be to pressurize the cuff to a supra-systolic pressure which is known to exceed, by a reasonable safety margin, the maximum value which the patient's intra-operative systolic blood pressure might reach. One difficulty with this approach is that, because the tourniquet cuff pressure is held constant throughout the surgical procedure at a pressure selected to account for a possible rise in the patient's systolic blood pressure to a "worst case" high pressure, the cuff may, for a substantial period of time, be pressurized well above the minimum pressure required to maintain a bloodless surgical field. This is an unnecessary hazard, and may be of particular concern in the case of some patients such as infants, small children, or adults with thin limbs having little protective musculature who may be particularly susceptible to injury caused by cuff over-pressurization.

A preferred approach, which overcomes the foregoing difficulty, is to vary the cuff pressure in response to variations in the patient's intra-operative systolic blood pressure, thereby maintaining a substantially constant pressure difference between the cuff pressure and the patient's systolic blood pressure. The pressure difference is selected so that the cuff is pressurized above the patient's systolic blood pressure but near the minimum supra-systolic pressure required to maintain a bloodless surgical field.

In implementing this preferred approach, the present invention provides a pneumatic tourniquet which senses the patient's systolic blood pressure during surgical procedures and which regulates the tourniquet cuff pressure as a function of the patient's intra-operative systolic blood pressure to maintain the cuff pressure near the minimum supra-systolic pressure required to maintain a bloodless surgical field. In other words, the cuff pressure is "adapted" to the patient's systolic blood pressure so as to maintain cuff pressure approximately near the minimum pressure required to provide a bloodless surgical field.

Ideally, cuff pressure is regulated as a function of the patient's intra-operative systolic blood pressure in accordance with the "preferred approach" described above. However, if the patient's blood pressure cannot reliably be sensed with accuracy then it would be undesirable to rely upon a sensed value of systolic blood pressure as a guide to regulation of tourniquet cuff pressure.

If the sensed blood pressure is unreliable, then an alternative to "adaptive" cuff pressure regulation is to fall back to the first approach described above and to maintain the cuff pressure relatively constant near a selected pressure (for example, within about 4 mmHg of a pressure in the 200–400 mmHg range). Thus, the present invention also provides a pneumatic tourniquet capable of automatically sensing and regulating cuff pressure to maintain the cuff pressure near a selected pressure.

SUMMARY OF THE INVENTION

The invention is directed to a pneumatic tourniquet for maintaining occluded or restricted blood flow into a patient's limb. The tourniquet comprises an inflatable cuff, pressurizing means for pressurizing the cuff, pressure relief means for depressurizing the cuff, blood pressure sensing means for sensing the patient's systolic blood pressure and for producing a blood pressure output signal representative of the systolic blood pressure, and pressure regulator means responsive to the blood pressure output signal for selectably activating ("adapting") the pressurizing means and the pressure relief means to maintain the cuff pressure above the patient's systolic blood pressure.

Preferably, the pneumatic tourniquet further comprises cuff pressure sensing means for sensing the cuff pressure and for producing an output signal representative thereof. The pressure regulator means may comprise electronic sensing and control apparatus for comparing the blood pressure and cuff pressure output signals, for producing a pressure decrease output signal to actuate the pressure relief means and depressurize the cuff if the cuff pressure exceeds an upper pressure limit, and for producing a pressure increase output signal to actuate the pressurizing means to pressurize the cuff if the cuff pressure is below a lower pressure limit.

In the "adaptive" mode of operation, the pressure regulator means varies the cuff pressure in response to variations in the patient's systolic blood pressure, thereby maintaining a substantially constant pressure difference between the cuff pressure and the patient's systolic blood pressure. In the "constant" mode of operation, the pressure regulator means holds the cuff pressure near a pressure which the operator may pre-select. The patient's systolic blood pressure is not used to regulate cuff pressure in the constant mode.

In the preferred embodiment, if the cuff is to occlude blood flow into an arm of the patient, the upper pressure limit is about 94 mmHg above the patient's systolic blood pressure and the lower pressure limit is about 86 mmHg above the patient's systolic blood pressure. If the cuff is to occlude blood flow into a leg of the patient, the upper pressure limit is about 129 mmHg above the patient's systolic blood pressure, and the lower pressure limit is about 121 mmHg above the patient's systolic blood pressure. Advantageously, limb indicator means may be provided to indicate whether the cuff is to occlude blood flow into an arm or into a leg of the patient. The upper and lower cuff pressure limits may then be selected by operation of the limb indicator means.

Preferably, the pneumatic tourniquet also comprises blood pressure alarm means for producing a blood pressure alarm signal if the patient's systolic blood pressure falls below 80 mmHg or rises above 160 mmHg. An inhibit alarm means is preferably provided for producing an inhibit alarm signal if the blood pressure sensing means is unable to successively sense the patient's systolic blood pressure for more than about 3 minutes.

The blood pressure sensing means should sense the patient's systolic blood pressure at periodic intervals. Blood pressure fluctuation alarm means may then be provided for producing a blood pressure fluctuation alarm signal if the systolic blood pressure sensed during a particular time interval differs, by more than a selected amount, from the systolic blood pressure sensed during the immediately preceding time interval. The selected amount may be about 32 mmHg.

Upon production of any one of the blood pressure alarm signal, the inhibit alarm signal, or the blood pressure fluctuation alarm signal, the pressure regulator means is preferably rendered non-responsive to the blood pressure output signal and responsive to the cuff pressure output signal, thereby selectably activating the pressurizing means and the pressure relief means to maintain the cuff pressure near a selected pressure without regard to the patient's systolic blood pressure (i.e. the "adaptive" mode of operation is discontinued in favour of the "constant" mode of operation).

Advantageously, the cuff includes a tourniquet cuff segment for occluding blood flow into the patient's limb, and a blood pressure cuff segment for coupling to the blood pressure sensing means for sensing the patient's systolic blood pressure.

BRIEF DESCRIPTION OF THE DRAWINGS

FIGS. 5A through 5E are an electronic circuit schematic diagram for the microprocessor and related circuitry which controls the preferred embodiment. FIG. 5F illustrates the interconnection of those portions of the circuitry which are shown separately in FIGS. 5A through 5E.

FIGS. 6A and 6B are an electronic circuit schematic diagram for the control/display circuitry of the preferred embodiment. FIG. 6C illustrates the interconnection of those portions of the circuitry which are shown separately in FIGS. 6A and 6B.

FIGS. 7A through 7C depict a dual function cuff having a tourniquet cuff segment and a blood pressure sensing cuff segment.

DESCRIPTION OF THE PREFERRED EMBODIMENT

I. Introduction

Figure 1:
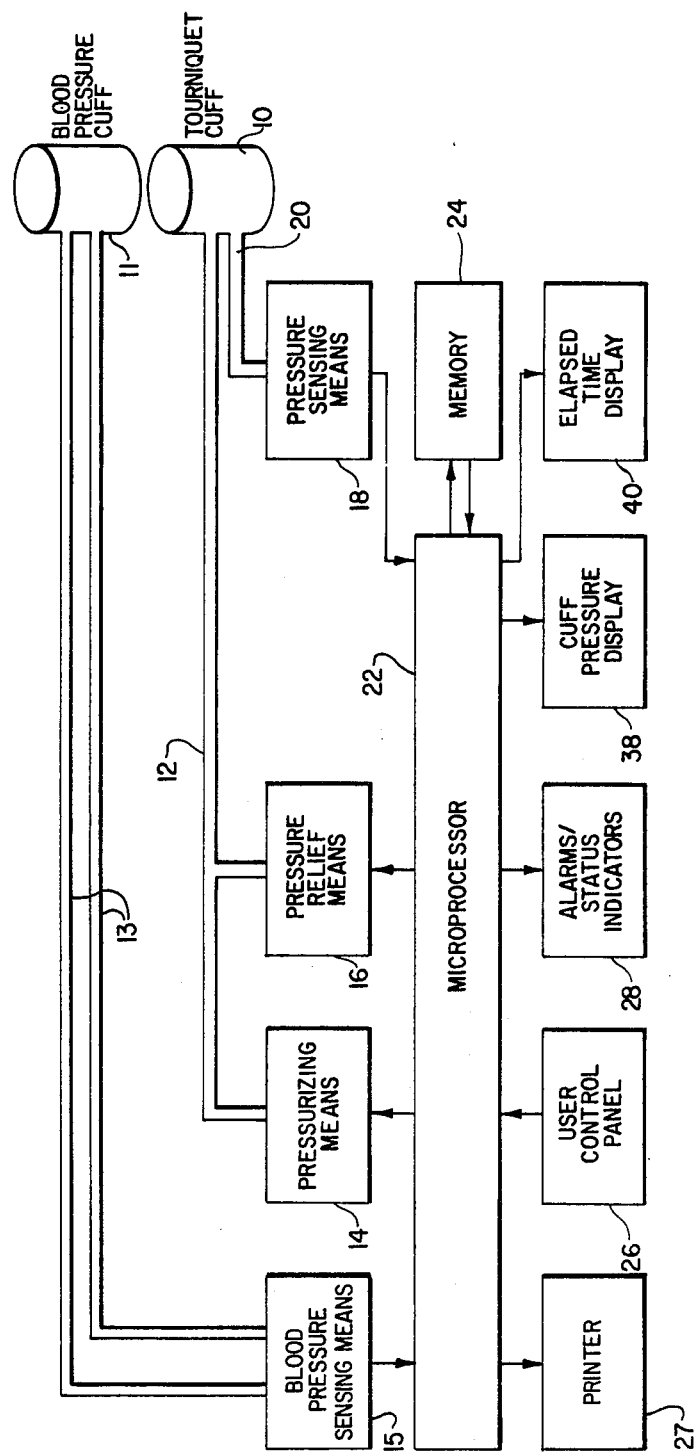
FIG. 1 is a block diagram of the preferred embodiment.

FIG. 1 is a block diagram which illustrates the operation of the preferred embodiment. An inflatable tourniquet cuff 10 which may be wrapped around a patient's limb is coupled via hose 12 to a pressurizing means 14 such as an electric air pump for pressurizing cuff 10. Hose 12 is also coupled to a pressure relief means 16 such as a normally closed valve which may be electronically opened to depressurize cuff 10. A cuff pressure sensing means 18 such as an electronic pressure transducer is coupled via hose 20 to a second port of cuff 10.

Blood pressure sensing cuff 11 is coupled via hoses 13 to blood pressure sensing means 15 which may be a commercially available blood pressure monitoring device such as a DINAMAP TM Model 845 non-invasive blood pressure monitor. Blood pressure sensing means 15 senses the patient's systolic blood pressure at periodic time intervals and produces a blood pressure output signal representative of the sensed systolic blood pressure. [The DINAMAP TM Model 845 blood pressure monitoring device does not directly "sense" the patient's systolic blood pressure. The device uses oscillometry techniques to periodically estimate the patient's mean arterial blood pressure, and employs an algorithm to extrapolate values of the patient's systolic and diastolic blood pressure. Other commercially available blood pressure monitoring devices (such as the VITA-STAT TM Model 900-S blood pressure monitor—which may use an auscultatory method to estimate systolic blood pressure, or other devices using infrasonde techniques) could be used as blood pressure sensing means 15. As used herein, the term "sensing" includes devices which estimate systolic blood pressure indirectly. Devices which measure blood pressure directly, for example, by insertion of a catheter in an arterial blood vessel, could also be used.]

Ideally, the pressure in cuff 10 is varied as a function of the patient's systolic blood pressure at the site where cuff 10 is applied. This is because the sensed value of the patient's systolic blood pressure may vary with a number of factors, including the distance from the heart at which the blood pressure measurement is made, the width of blood pressure sensing cuff 11 as compared with the limb circumference at the site where cuff 11 is applied, and the local limb geometry. Thus, the systolic blood pressure sensed in a patient's arm may differ significantly from the systolic blood pressure that might be sensed at the same time in the same patient's leg. Accordingly, it is desirable that blood pressure sensing cuff 11 be applied as closely as possible to tourniquet cuff 10 in order to minimize differences between the sensed value of the patient's systolic blood pressure (i.e. the value which will be used to adaptively vary the pressure in tourniquet cuff 10) and the value of the patient's systolic blood pressure at the site where tourniquet cuff 10 is applied (i.e. the value with respect to which the pressure in cuff 10 is ideally varied). For a variety of clinical reasons, this may not always be possible. Advantageously, however, in many instances tourniquet cuff 10 and blood pressure sensing cuff 11 may be combined in a "dual function cuff" having two cuff segments arranged as shown in FIGS. 7A through 7C. Hoses 12 and 20 may be connected to ports 23 in tourniquet cuff segment 17. Hoses 13 would be connected to ports 21 in blood pressure sensing cuff segment 19.

Tourniquet cuff segment 17 and blood pressure sensing cuff segment 19 are stitched together over only about one third of their total length (see FIG. 7A). Thus, the two segments may be independently fitted about a tapered limb to more closely conform the cuff fit to the limb geometry than would be possible if both segments were stitched together so that they had to be wrapped around the limb in a substantially cylindrical configuration.

FIG. 7B shows how each segment of the dual function cuff may be assembled. A plastic liner is fitted over an inflatable bladder and the two are then slipped inside a cuff envelope. Holes in the plastic liner and in the cuff envelope enable the cuff ports to protrude from the cuff segment. The plastic liner is positioned away from the side of the cuff segment which will be against the patient's skin. This is because the liner acts as a stiffener, tending to direct the pressure exerted by the inflated bladder inward to the patient's limb, rather than outward against the cuff envelope. The cuff envelope includes a strap which is folded back over the cuff ports (to the right in FIG. 7B) to the position shown in FIG. 7A. The strap and the outer surface of the cuff are lined with VELCRO TM so that the two may be releasably fastened together around the patient's limb. Ties are also provided to assist in fastening the cuff segment around the limb.

The dual function cuff reduces the labour intensive operations required to fit the patient with two separate cuffs and also reduces the total space obstructed by the cuffs. The latter advantage may be of particular significance if there is only one limb available for cuff application (i.e. since other limbs might be obstructed by intravenous lines, etc.).

Pressurizing means 14, blood pressure sensing means 15, pressure relief means 16 and cuff pressure sensing means 18 are electronically coupled to microprocessor 22 which has an associated memory 24.

A user control panel 26 is provided to enable the selection of various operating parameters. For example, a user may, with the aid of control panel 26, define a selected pressure to which cuff 10 is to be inflated when operating, as hereinafter described, in the "constant" mode, and a time period for which cuff 10 is to be pressurized.

Cuff pressure sensing means 18 produces a cuff pressure output signal which is representative of the pressure in cuff 10. Microprocessor 22 is pre-programmed (as hereinafter described) to compare the cuff pressure and blood pressure output signals and to produce a pressure decrease output signal for actuating pressure relief means 16 to depressurize cuff 10 if the cuff pressure exceeds an upper pressure limit, or to produce a pressure increase output signal for actuating pressurizing means 14 to pressurize cuff 10 if the cuff pressure falls below a lower pressure limit. For example, in the preferred embodiment, if cuff 10 is to occlude blood flow into a patient's arm, the upper pressure limit is about 94 mmHg above the patient's systolic blood pressure and the lower pressure limit is about 86 mmHg above the patient's systolic blood pressure (i.e. the cuff pressure is maintained 90 mmHg ±4 mmHg above the patient's systolic blood pressure). If cuff 10 is to occlude blood flow into a patient's leg, then the upper pressure limit is preferably about 129 mmHg above the patient's systolic blood pressure and the lower pressure limit is about 121 mmHg above the patient's systolic blood pressure (i.e. the cuff pressure is maintained 125 mmHg ±4 mmHg above the patient's systolic blood pressure). Microprocessor 22 is also pre-programmed to monitor the cuff pressurization time period.

A number of alarm/status indicators 28 provide the operator with information respecting the operating status of the pneumatic tourniquet as well as visual and audible alarms to warn the operator of hazardous conditions such as pressurization of cuff 10 for, or in excess of the selected cuff pressurization time period. The operator is provided with a digital readout of the instantaneous pressure in cuff 10 at cuff pressure display 38 and of the elapsed time during which cuff 10 has been pressurized at elapsed time display 40.

Printer 27 is electronically coupled to microprocessor 22. Printer 27 serves as a recorder means for periodically recording the operational status of the pneumatic tourniquet. For example, periodic, contemporaneous records of the sensed value of the patient's systolic blood pressure and of the pressure in cuff 10 may be printed on printer 27. The records may also include an indication of the time at which each periodic contemporaneous record is made, a message to indicate whether the pressure regulator means is operating in response to the blood pressure output signal (i.e. in the "adaptive" mode) or in response to the cuff pressure output signal (i.e. in the "constant" mode), and messages to indicate whether any alarms have been triggered. In the preferred embodiment, printer 27 is a DINAMAP™ Model 950 trend recorder.

The preferred embodiment will first be described from the point of view of a typical user such as an operating room nurse or technician. A technical description of the construction and operation of the preferred embodiment will then be provided, followed by a discussion of the software programming for the microprocessor used in the preferred embodiment.

II. Operation by Typical User

Figure 2:
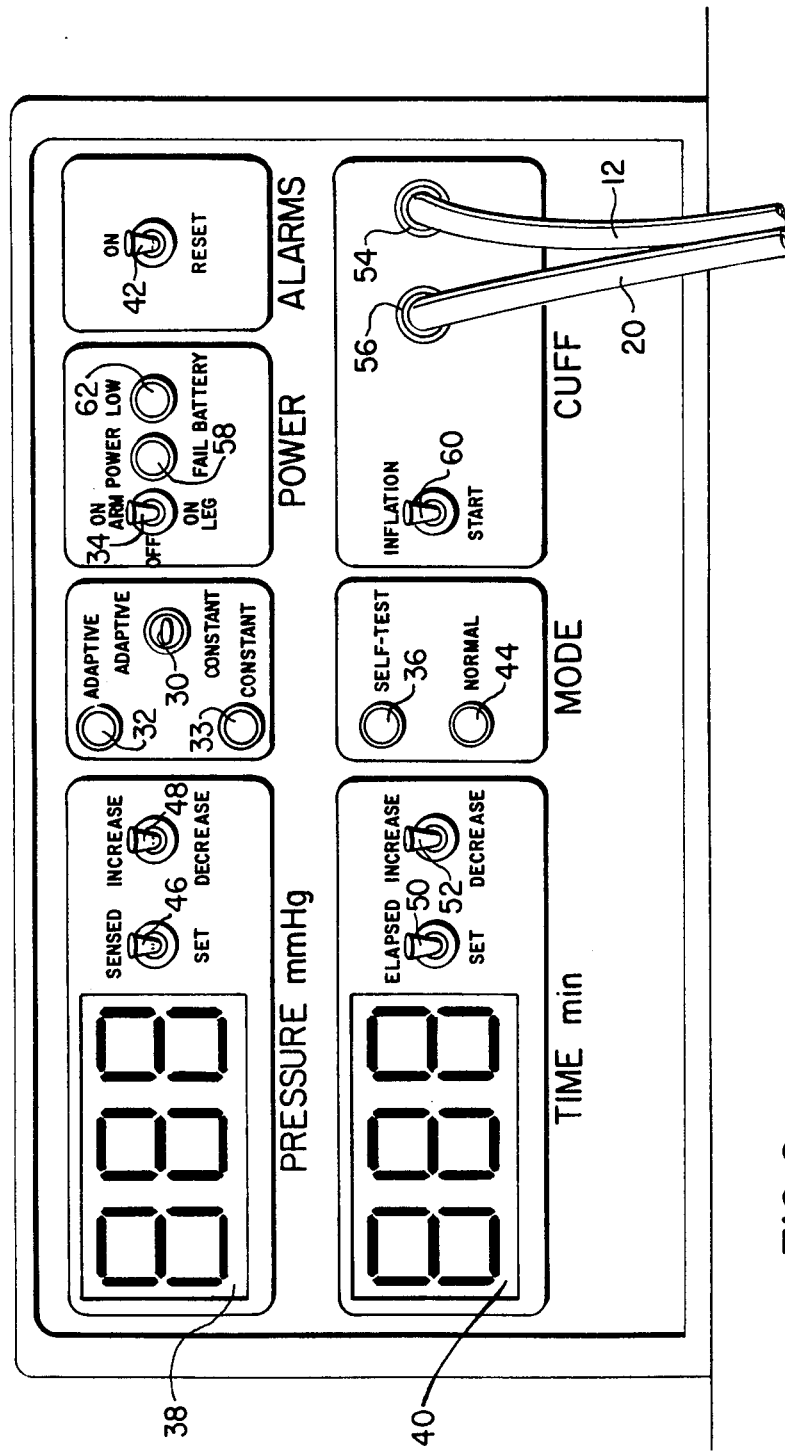
FIG. 2 is a pictorial representation of a control/display panel for the preferred embodiment.

FIG. 2 shows a control/display panel for the pneumatic tourniquet. The AC power plug (not shown) of the device is connected to an AC power receptacle and the pneumatic tourniquet is activated by moving switch 34 from the "off" position to either the "on-arm" position (if cuff 10 is to occlude blood flow into the patient's arm) or the "on-leg" position (if cuff 10 is to occlude blood flow into the patient's leg). Switch 34 serves as a "limb indicator means" for indicating whether cuff 10 is to occlude blood flow into an arm or into a leg of the patient. In the preferred embodiment, the aforementioned upper and lower cuff pressure limits are automatically selected by operation of switch 34. For example, if switch 34 is turned to the "on-arm" position the upper and lower pressure limits are set, respectively, to 94 and 86 mmHg above the patient's systolic blood pressure.

Instead of a limb indicator means such as switch 34, different tourniquet cuff couplers might be provided to uniquely identify whether cuff 10 is to be used on an arm or on a leg. Each coupler could have a characteristic, detectable by microprocessor 22, which would indicate whether cuff 10 was to occlude blood flow into an arm or a leg of the patient. For example, separate leg cuff couplers and arm cuff couplers could be provided on user control panel 26. The leg cuff couplers on the user control panel would be capable of mechanical coupling only with mating couplers on a "leg cuff". Similarly, the arm cuff couplers on the user control panel could be mechanically coupled only with mating couplers on an "arm cuff".

When switch 34 is turned to either "on" position, the pneumatic tourniquet automatically enters a "self-test" mode of operation which is indicated by the illumination of indicator light 36. The self-test mode of operation enables the operator to verify that the device is operating properly.

(a) Self Test Mode of Operation

In the self-test mode, pressure display 38 and time display 40 (which are each three digit 7-segment light emitting diode displays) are each caused to display the numerals "888" so that the operator may verify that all display segments are functioning. An audible alarm (not shown in FIG. 2) is also sounded so that the operator may verify that it is working properly.

The operator should then disconnect the AC power plug from the receptacle and ensure that power fail indicator light 58 is thereby illuminated. The AC plug is then reconnected, which should extinguish indicator light 58.

Once the operator has verified the correct operation of displays 38 and 40, power fail indicator light 58 and the audible alarm, he may momentarily depress switch 42 to the "reset" position to terminate the self-test sequence and enter the "normal" mode of operation (switch 42 normally remains in the "on" position depicted in FIG. 2). When the normal mode of operation is entered self-test mode indicator light 36 is extinguished and normal mode indicator light 44 is illuminated.

(b) Normal Mode of Operation

The normal mode of operation is divided into two sub-modes—the "adaptive" mode of operation, and the "constant" mode of operation. In the adaptive mode, the pressure in cuff 10 is regulated as a function of the patient's intra-operative systolic blood pressure in response to the blood pressure output signal produced by blood pressure sensing means 15. In the constant mode, the pressure in cuff 10 is maintained at or near a pressure which is pre-selected by the operator, and which is not varied in response to intra-operative changes in the patient's systolic blood pressure. In the constant mode, the pressure in cuff 10 is changed only in response to variations in the cuff pressure output signal produced by pressure sensing means 18.

Operation of the pneumatic tourniquet always begins in the constant mode. Once cuff 10 has been pressurized to the pressure pre-selected by the operator, the adaptive mode may be entered by manually moving switch 30 momentarily from its normal centre position to the "adaptive" position. The pneumatic tourniquet may be caused to revert from the adaptive to the constant mode of operation either automatically (by microprocessor 22, as described hereinafter) or manually (by momentarily moving switch 30 from its normal centre position to the "constant" position).

Indicator light 32 is illuminated when the pneumatic tourniquet is operating in the adaptive mode. If operation automatically reverts to the constant mode (by action of microprocessor 22), indicator light 32 is flashed on and off, indicator light 33 is illuminated, the audible alarm sounds and a message is printed on recorder 27 to indicate the change of mode. Alternatively, if operation reverts manually to the constant mode (by operation of switch 30) indicator light 32 is extinguished, indicator light 33 is illuminated, and a message is printed on recorded 27 to indicate the change of mode, but the audible alarm does not sound.

The operator first selects a nominal pressure to which tourniquet cuff 10 is to be initially pressurized before the adaptive mode of operation is entered. This is the pressure near which cuff 10 will be held in the constant mode of operation.

To select the initial cuff pressure, the operator depresses switch 46 to the "set" position shown in FIG. 2. A pre-selected nominal pressure of 200 mmHg will appear in display 38 if switch 34 is in the "on-arm" position. A pre-selected nominal pressure of 275 mmHg will appear in display 38 if switch 34 is in the "on-leg" position. While continuing to depress switch 46, the operator may then either raise or lower the selected cuff pressure with respect to the pre-selected nominal level by moving switch 48 to the "increase" position (if a selected pressure greater than the nomimal level is desired) or to the "decrease" position (if a selected pressure less than the nominal level is desired). When switch 48 is in the "increase" position, the pressure appearing in display 38 will gradually increase to a maximum of 400 mmHg. When switch 48 is in the "decrease" position, the pressure appearing in display 38 will gradually decrease to a minimum of 0 mmHg. When the selected cuff pressure appears in display 38, switch 46 is released. Note that two separate switches must be operated to select the cuff pressure. This is a safety feature intended to prevent inadvertent alteration of the selected cuff pressure. When switch 46 is released it returns to the "sensed" position, and display 38 provides the operator with a continual digital readout of the pressure to which cuff 10 is inflated (initially, this will be "0").

The operator then selects, in similar fashion, the cuff pressurization time period—the estimated time for which cuff 10 is to be pressurized. Switch 50 is depressed to the "set" position shown in FIG. 2 and a pre-selected nominal time period of 60 minutes appears in display 40. While continuing to depress switch 50, the operator may either increase or decrease the cuff pressurization time period with respect to the nominal 60 minute time period by moving switch 52 to the "increase" position (if it is desired that cuff 10 be pressurized for a period in excess of 60 minutes) or to the "decrease" position (if it is desired to pressurize cuff 10 for a period of time less than 60 minutes). In either case, the time presented in minutes at display 40 will gradually increase (to a maximum of 180 minutes) or decrease (to a minimum of 0 minutes). When the selected time period appears in display 40, the operator releases switches 50 and 52. Again, as a safety feature, two separate switches are required to set the cuff pressurization time period to avoid inadvertent alteration thereof. When switch 50 is released it returns to the "elapsed" position and display 40 provides the operator with a continual digital readout of the time period during which cuff 10 has been pressurized (initially, a time period of "0" is displayed).

The patient's limb is prepared and cuffs 10 and 11 applied thereto in accordance with established medical procedures. Blood pressure cuff 11 is applied to the limb in a position which is proximal to tourniquet cuff 10. (This assumes that both cuffs 10 and 11 are applied to the same limb. Blood pressure sensing cuff 11 may be applied to a limb other than that to which tourniquet cuff 10 is applied although, as previously discussed, it is desirable that blood pressure sensing cuff 11 be applied as closely as possible to tourniquet cuff 10.)

Hose 12 couples an air inlet port of cuff 10 to pressurizing means 14 and to pressure relief means 16 via port 54 shown in FIG. 2. Hose 20 couples an air outlet port of cuff 10 to pressure sensing means 18 via port 56 shown in FIG. 2. Preferably, separate supply and return hoses are used to convey pressurized air to and from cuff 10. Such a "dual-line" cuff may facilitate the detection of "kinks" or occlusions in the hoses. However, if a conventional single-port cuff must be used then an appropriate "Y" type adaptor should be used to couple a single hose from the cuff to ports 54 and 56.

Once the initial cuff pressure and the cuff pressurization time period have been selected, switch 60 is momentarily depressed to the "start" position to actuate pressurizing means 14 and pressurize tourniquet cuff 10. Instantaneous values of the pressure in cuff 10 (expressed in mmHg) appear in display 38. When switch 60 is depressed to the "start" position, an elapsed-time clock is automatically activated to "count" the cuff pressurization time period, and instantaneous values of elapsed time (in minutes) appear in display 40. At this point, the device is in the constant mode of operation and automatically regulates the pressure in cuff 10 (as hereinafter described) to maintain it within about 4 mmHg of the selected cuff pressure. The operator should then activate blood pressure sensing means 15 and ensure that reasonable measurements of systolic blood pressure are obtained (the DINAMAP TM Model 845 blood pressure monitor used in the preferred embodiment prints these measurements directly on recorder 27). To change from the constant to the adaptive mode of operation, switch 30 is moved from its normal centre position to the "adaptive" position and the device then regulates the pressure in cuff 10 as a function of the patient's intra-operative systolic blood pressure as determined by blood pressure cuff 11 and blood pressure sensing means 15. In the adaptive mode, the pressure in cuff 10 is preferably maintained at about 86-94 mmHg above the patient's systolic blood pressure if cuff 10 is to occlude blood flow into an arm (as determined by the setting of switch 34). A somewhat higher pressure above systolic may be required to effectively occlude blood flow into a leg. Thus, in the adaptive mode, the pressure in cuff 10 is preferably maintained at about 121-129 mmHg above the patient's systolic blood pressure if cuff 10 is to occlude blood flow into a leg.

To deflate cuff 10 upon completion of the surgical procedure switches 46 and 48 are used to set the selected cuff pressure to a "zero" value. Cuff 10 then deflates to zero pressure as soon as switch 46 is released. Once cuff 10 has deflated switch 34 should be moved to the "off" position and cuffs 10 and 11 removed from the patient.

(c) Alarms

Three alarms, namely, a "blood pressure alarm", an "inhibit alarm" and a "blood pressure fluctuation alarm" may be triggered while the device is operating in the adaptive mode. If any of these three alarms are triggered, operation of the pneumatic tourniquet is automatically switched by microprocessor 22 from the adaptive to the constant mode, resulting in the alarm indications noted previously. Momentarily depressing switch 42 to the "reset" position will clear the alarm condition.

The blood pressure alarm is triggered if the patient's systolic blood pressure, as sensed by blood pressure sensing means 15, is either below 80 mmHg or above 160 mmHg. Either extreme may represent an abnormal condition in the patient requiring medical attention. These limits however are somewhat arbitrary at present and may be revised as clinical experience is gained.

The inhibit alarm is triggered if blood pressure sensing means 15 is unable to make successive measurements of the patient's systolic blood pressure for more than about 3 minutes, which may be indicative of a malfunction of blood pressure sensing means 15, or the presence of physiologic or environmental conditions which prevent blood pressure sensing means 15 from functioning properly.

The blood pressure fluctuation alarm is triggered if the systolic blood pressure sensed by blood pressure sensing means 15 during a particular time interval differs, by more than a selected amount, (preferably about 32 mmHg) from the systolic blood pressure sensed during the immediately preceeding time interval. Since blood pressure sensing means 15 is programmed, in the preferred embodiment, to normally sense the patient's systolic blood pressure about once every minute, a 32 mmHg change represents a significant alteration and may be indicative of a change in the patient's physiologic status, or a malfunction of blood pressure sensing means 15, either of which may require attention.

If blood pressure sensing means 15 becomes incapable of providing reliable measurements of the patient's systolic blood pressure then, as indicated above, the device automatically reverts from the adaptive to the constant mode of operation and holds the pressure of cuff 10 near the pre-selected pressure. This is accomplished by discontinuing the regulation of the pressure in cuff 10 in response to the blood pressure output signal produced by blood pressure sensing means 15 (i.e. the adaptive mode is terminated) and by regulating the cuff pressure only in response to changes in the cuff pressure output signal produced by pressure sensing means 18 (i.e. the constant mode is activated).

The remaining alarms may be triggered whether the device is operating in the adaptive or constant modes.

Microprocessor 22 periodically activates pressurizing means 14 or pressure relief means 16 to minutely increase or decrease the pressure in cuff 10. Such minute variations have no significant effect upon the occlusion of blood flow into the patient's limb, but they are detectable by pressure sensing means 18. A characteristic change in the pressure of cuff 10 should occur upon activation of either pressurizing means 14 or pressure relief means 16, depending upon the pre-activation pressure of cuff 10 and the time during which pressurizing means 14 or pressure relief means 16 is activated. If the expected characteristic change is not detected by microprocessor 22 (via pressure sensing means 18), a cuff pressure alarm is triggered by sounding the audible alarm and by flashing on and off the cuff pressure which appears in display 38. The operator should examine hoses 12 and 20 for kinks or occlusions which may prevent free passage of pressurized air to or from cuff 10. Cuff 10, hoses 12 and 20, and the various connectors should also be checked for damage, leaks or obstructions. The cuff pressure alarm is automatically deactivated upon correction of the problem which triggered the alarm.

A time alarm is triggered if cuff 10 remains pressurized for, or in excess of the selected cuff pressurization time period. If the time alarm is triggered, the audible alarm sounds and display 40 flashes on and off to draw the operator's attention to the excess period of cuff pressurization. The cuff is not deflated. To deactivate the time alarm in order to complete a procedure the operator may increase the cuff pressurization time period to a new value up to a maximum of 180 minutes from commencement of the "count".

A power alarm is triggered upon interruption of external AC power supplied to the device. If AC power is interrupted the audible alarm sounds and indicator light 58 is illuminated. In the event of an AC power failure, an internal battery is automatically used to supply power to at least pressure sensing means 18 and the electronic circuitry so that cuff 10 is not deflated and so that the operator may continue to monitor the cuff pressure and the elapsed time. The power alarm is automatically deactivated upon reconnection of AC power to the device.

A battery alarm is triggered, sounding the audible alarm and illuminating indicator light 62 if the output voltage of an internal backup battery falls below a predetermined threshold (which, in the preferred embodiment, is 10.2 volts) indicating that the battery may be able to power the device for only a short period of time. If the battery alarm is triggered the device should immediately be connected to an AC power source to recharge the battery. The battery alarm is automatically deactivated once the battery has been recharged.

The audible portion of any of the alarms may be temporarily deactivated by depressing switch 42 to then "reset" position. This action will deactivate the audible alarm for 30 seconds but will not deactivate any visual alarm indicator. The blood pressure alarm, the inhibit alarm and the blood pressure fluctuation alarm are self-correcting and self-deactivating in the sense that operation switches from the adaptive to the constant mode, thus circumventing the problems represented by those alarms. The remaining alarms are not permanently deactivated until correction of the problem which triggered the alarm.

Figure 3:
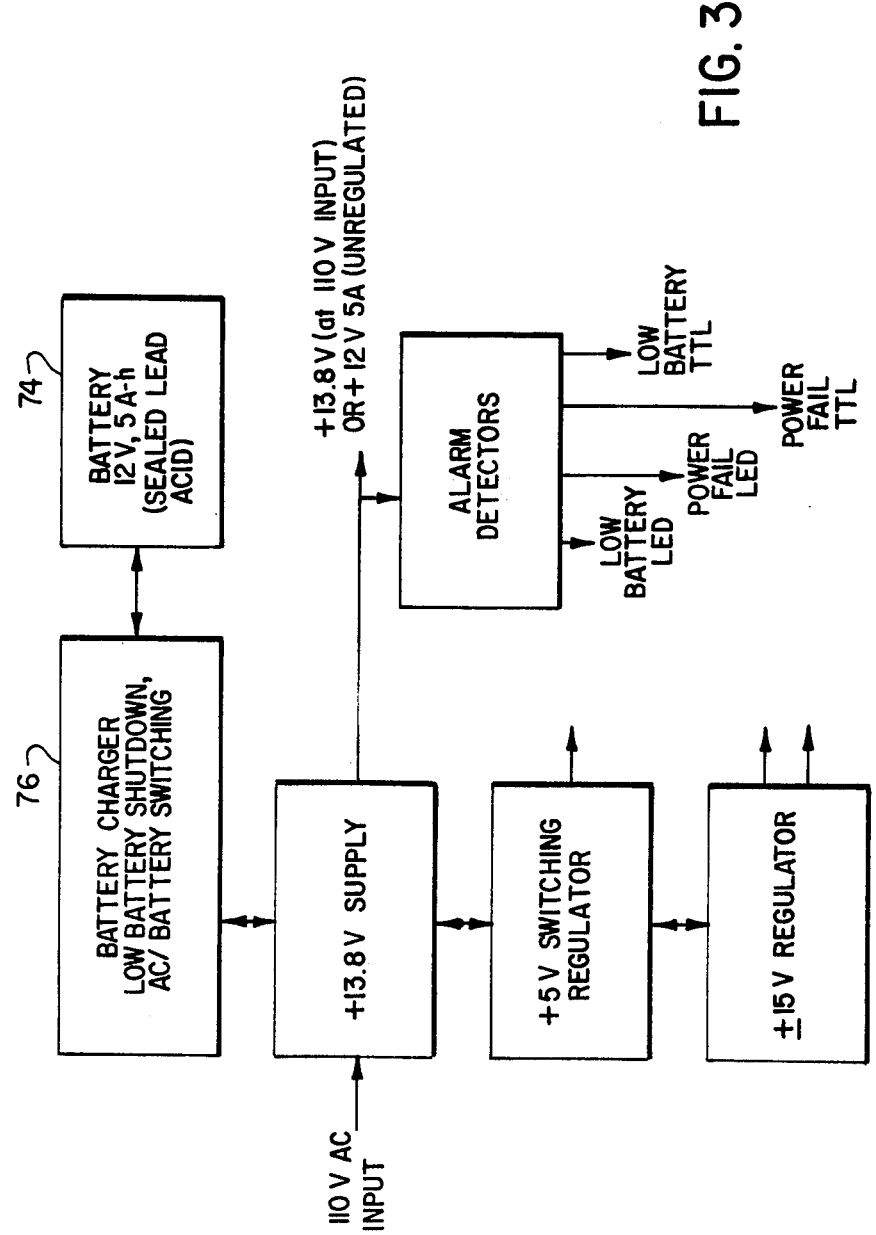
FIG. 3 is a block diagram of a power supply for the preferred embodiment.

III. Construction and Technical Operation (a) Power Supply and Backup Battery FIG. 3 depicts the power supply, backup battery and battery charger in block diagram form. The power supply converts an externally supplied 110 volt AC input signal into DC outputs of +13.8 volts (or +12 volts of unregulated power if the backup battery is used), +5 V, +15 V, and −15 V.

Figure 4:
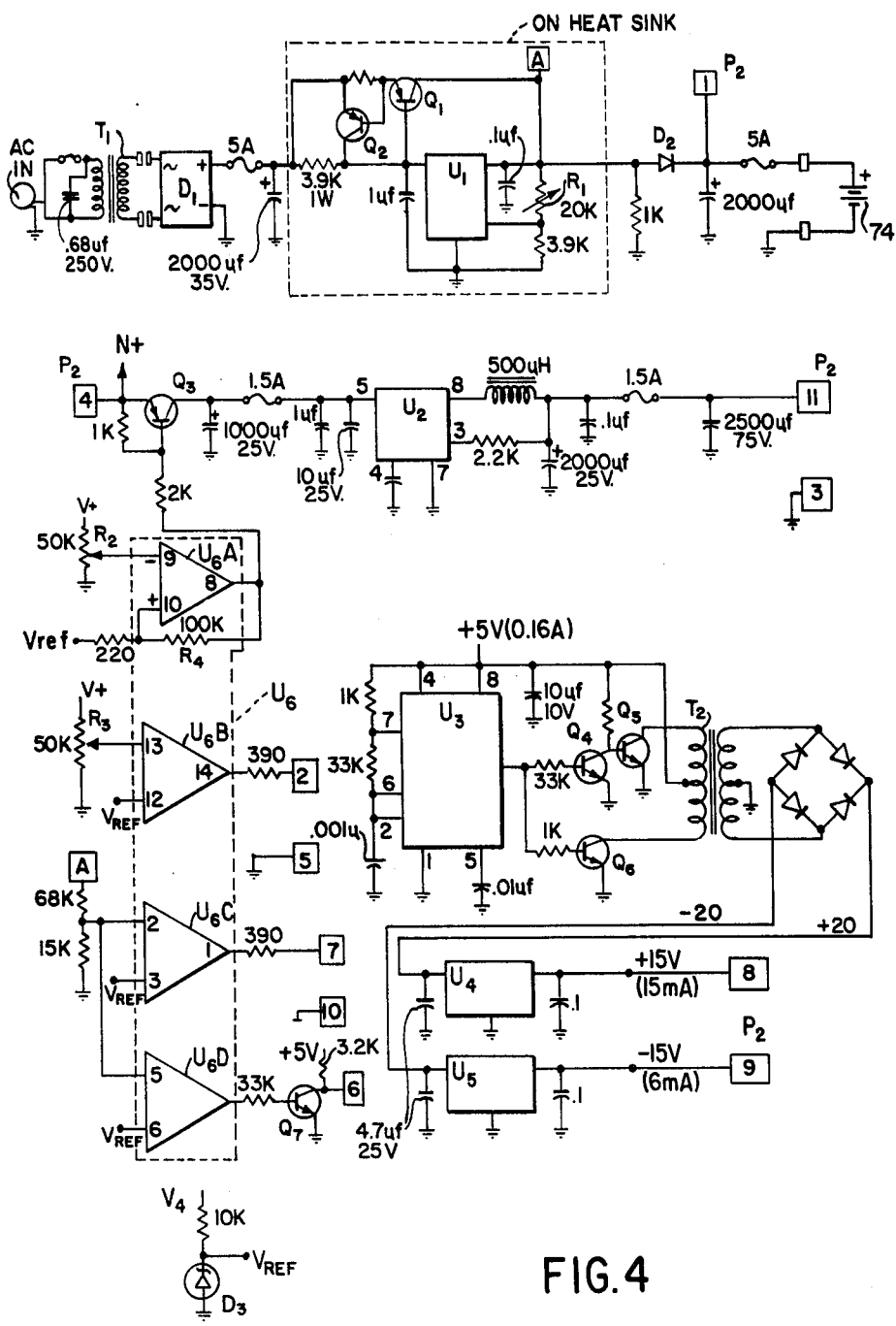
FIG. 4 is an electronic circuit schematic diagram of a power supply, backup battery and battery charging circuit for the preferred embodiment.

Backup battery 74 is a 12-volt, 5 amp-hour battery of the sealed lead-acid type. A charging circuit 76 is provided to maintain the voltage across the terminals of battery 74 at about +13.8 volts when the device is connected to a 110 volt AC power source. FIG. 4 is an electronic circuit schematic diagram of the power supply circuit, backup battery and battery charging circuitry.

Transformer $T_1$ steps the 110 volt AC supply voltage down to 16 volts which is then rectified by diode bridge rectifier $D_1$. Voltage regulator $U_1$ and pass transistor $Q_1$ regulate the voltage to +13.8 volts for presentation at the terminals of battery 74. Transistor $Q_2$ limits the current applied to battery 74 to approximately 3 amps to avoid overcharging the battery. Diode $D_2$ prevents battery current flowing back into voltage regulator $U_1$.

Variable resistor $R_1$ is used to adjust the voltage at the terminals of battery 74 to +13.8 volts when a 110-volt AC power supply signal is presented at the input terminals of transformer $T_1$. A battery charging voltage of +13.8 volts permits each cell of battery 74 to be charged at a constant voltage of 2.3 volts. A regulated source of +13.8 volts is thus available at pin 1 of connector $P_2$ if a 110-volt AC input signal is presented at the input terminals of transformer $T_1$. If an AC input signal is not present then +12 volts of unregulated power (derived from battery 74) is provided at pin 1 of connector $P_2$. Pin 1 of connector $P_2$ is coupled to pin 4 of connector $P_2$, when switch 34 is in either "on" position, to supply power to other portions of the power supply circuit.

Switching regulator $U_2$ provides high efficiency step-down regulation of the +13.8 volt (or +12 volt) supply signal to +5 volts. The +5 volt signal is used to power microprocessor 22 and its associated memories, as well as the analog to digital converter, timer, display drivers, indicator lights and audible alarm, all of which are hereinafter described.

Oscillator $U_3$ and transistors $Q_4$, $Q_5$ and $Q_6$ drive a step-up toroidal transformer $T_2$ at 20 kHz. The secondary output of transformer $T_2$ is rectified and regulated to $\pm 15$ volts by voltage regulators $U_4$ and $U_5$ respectively. The $\pm 15$ volt supply is used to power pressure sensing means 18 and its associated processor circuitry (hereinafter described).

A quad operational amplifier $U_6$ is used in a voltage comparator mode to provide "low battery", "power fail" and "battery shut-down" signals. A temperature compensated high precision reference diode $D_3$ provides a voltage reference for the voltage comparators.

Variable resistor $R_2$ is adjusted to shut off the driving signal presented by voltage comparator $U_6A$ to switching Darlington transistor $Q_3$ if the voltage at the output terminals of battery 74 falls below the threshold of 10.2 volts. $Q_3$ will thus disconnect battery 74 to prevent it from completely discharging. Resistor $R_4$ adds a slight hysteresis to avoid operating transistor $Q_3$ in its linear region.

Variable resistor $R_3$ is adjusted so that voltage comparator $U_6B$ will produce a "low battery" output signal if the voltage across the terminals of battery 74 falls below a threshold of 11.4 volts. This signal is used to drive low battery indicator light 62 shown in FIG. 2 and to provide a TTL logic level suitable for input to microprocessor 22.

Voltage comparators $U_6C$ and $U_6D$ are used to detect the absence of the 110 volt externally supplied AC power signal, to drive power fail indicator light 58 shown in FIG. 2 and to provide a TTL logic signal suitable for input to microprocessor 22 as hereinafter described.

The following parts list provides details of components used in constructing the power supply shown in FIG. 4. All resistors and capacitors not listed below are standard components with values as shown in FIG. 4.

| ITEM | DESCRIPTION | QUANTITY |
|---|---|---|
| Circuit breaker | Potter & Brumfield 37-401-101 | 1 |
| $D_1$ | Motorola MDA-970-21 | 1 |
| Battery | Gates 2V, 5A-h, 0800-0004 | 6 |
| $D_2$ | Motorola 1N5402 | 1 |
| $Q_1$, $Q_2$ | Motorola MJE2955 | 2 |
| $Q_3$ | Motorola TIP 126 | 1 |

-continued

| ITEM | DESCRIPTION | QUANTITY |
|---|---|---|
| $Q_4$, $Q_5$, $Q_6$ | Motorola 2N3904 | 3 |
| $Q_7$ | Motorola 2N4123 | 1 |
| $T_1$ | Hammond 166M16 | 1 |
| $T_2$ | Toroid, ⅞" OD, 50T/260T, #26 AWG | 1 |
| $U_1$ | Fairchild uA78G | 1 |
| $U_2$ | Fairchild SH1605 | 1 |
| $U_3$ | Motorola MC1455 | 1 |
| $U_4$ | Motorola 78L15 | 1 |
| $U_5$ | Motorola 79L15 | 1 |
| $U_6$ | National LM324 | 1 |
| $D_3$ | National LM113H | 1 |

(b) Pressurizing Means

In the preferred embodiment, pressurizing means 14 comprises a WISA 12 volt D.C. airpump. This is a motor offset cam diaphragm pressure generator which operates from a 12 volt D.C. power supply. The pump is capable of generating a maximum cuff pressure of about 600 mmHg. It has been suggested that cuff pressures no greater than about 400 mmHg should be adequate to maintain a bloodless surgical field. [See: L. Klenerman and G. H. Hulans, Tourniquet Pressures for the Lower Limb, *J. Bone Joint Surg.*, 61B:124, 1979; and, R. Sanders, The Tourniquet: Instrument or Weapon? *Hand*, 5:119-123, 1973].

(c) Pressure Relief Means

In the preferred embodiment, pressure relief means 16 comprises a Clippard EVO-3-12 electronic valve. This is a normally open, 3-way poppet valve having a poppet travel of 0.010 inches, pressure range of 0-105 psi, air flow of 0.5 cfm. at 100 psi., and a response time of 5 ms at 100 psi. A +12 volt DC signal is used to actuate the valve which consumes about 0.65 watts.

(d) Pressure Sensing Means

In the preferred embodiment, pressure sensing means 18 comprises a National Semiconductor LX1702GN electronic pressure transducer shown at 88 in FIG. 6B. Cuff 10 is coupled via hose 20 and port 56 (FIG. 2) to the inlet port of pressure transducer 88. Pressure transducer 88 produces an output voltage in the 2.5-12.5 volt range which corresponds to pressures of 0-760 mmHg. Three amplifiers 90, 92 and 94 (FIG. 6B) of a National Semiconductor LM324A quad operational amplifier shift and scale the transducer output voltage into the 0-5 volt range for presentation to analog to digital converter 84 which may be seen in FIG. 5A. In the preferred embodiment, analog to digital converter 84 is a National Semiconductor ADC0816 integrated circuit.

The pressure transducer output voltage should be calibrated after the device has been powered in the "normal" mode of operation for about 5 minutes. With a cuff pressure of 0 mmHg (achieved by disconnecting hoses 12 and 20 from cuff 10) variable resistor $R_5$ (FIG. 6B) is adjusted so that the output voltage of operational amplifier 92 is within 0.010 volts of 0.000 volts. The cuff pressure should then be increased to 300 mmHg (by using "T" adaptors to connect pressure transducer 88 to an external pressure source and to a pressure gauge having an error of less than 1%) and variable resistor $R_6$ adjusted so that the output of operational amplifier 92 is within 0.010 volts of 2.930 volts.

(e) Microprocessor and Digital Circuitry

Figure 5A:
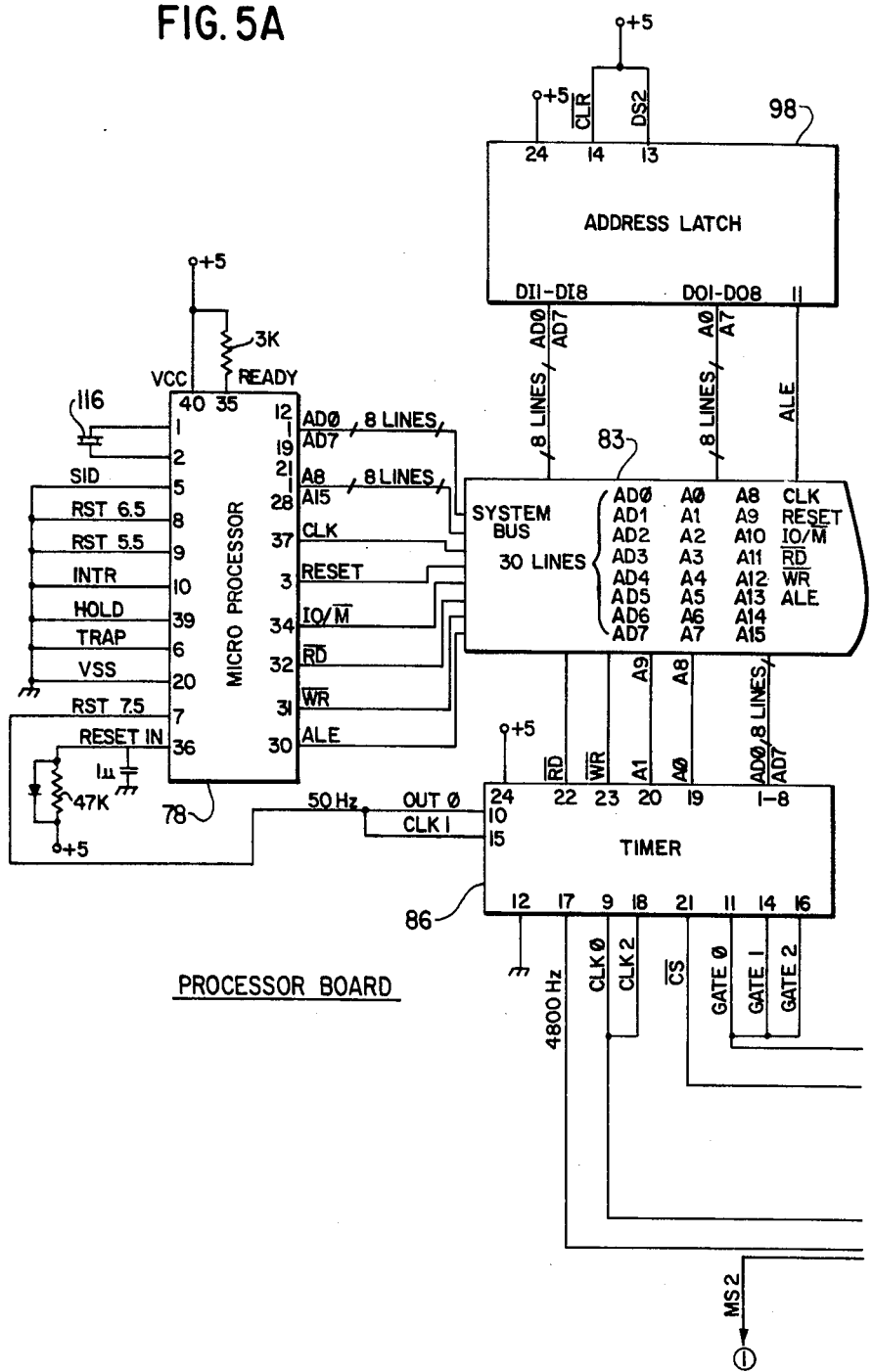
Figure 5B:
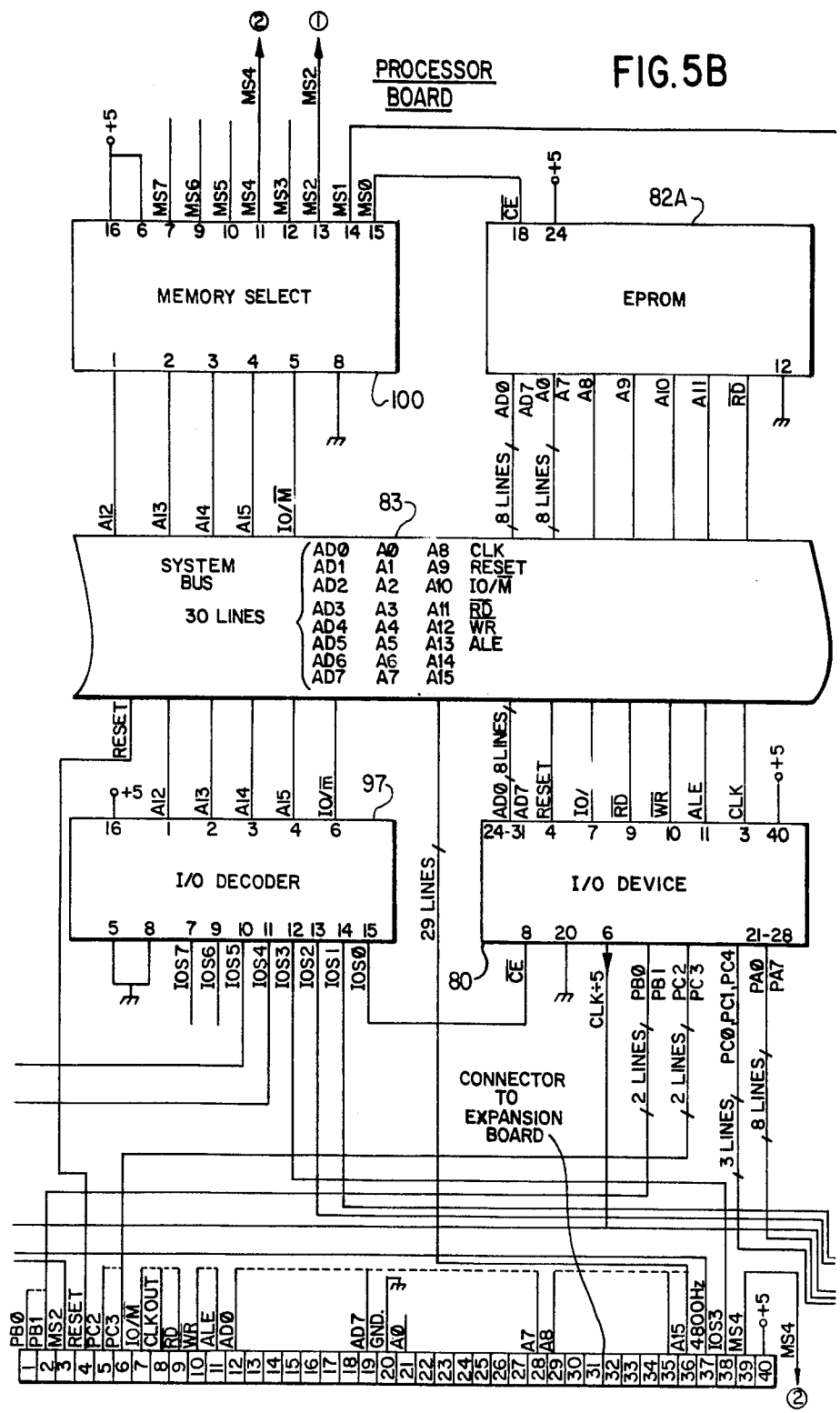
Figure 5C:
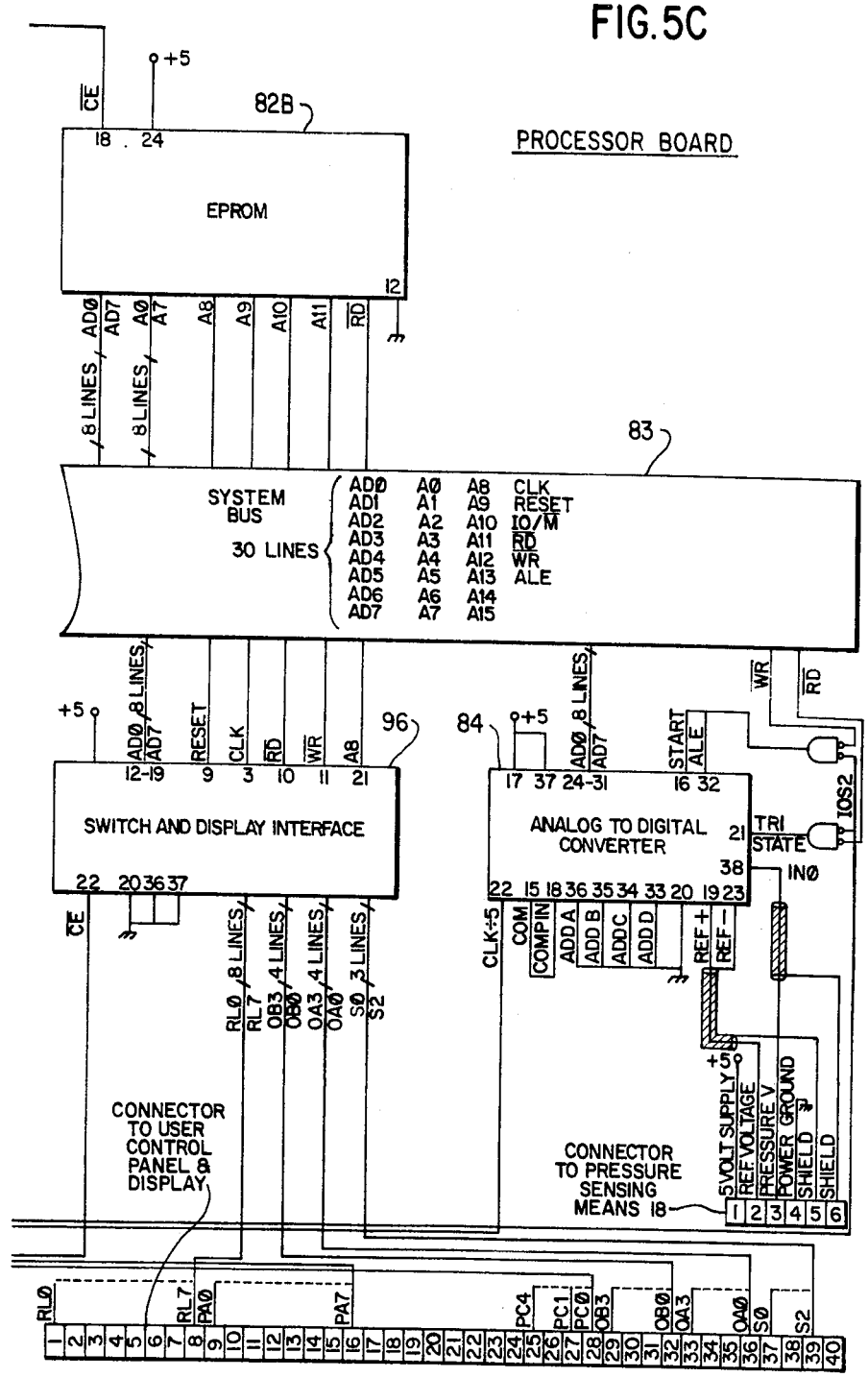

For clarity of illustration, the microprocessor and its related digital circuitry are shown separately in FIGS. 5A through 5E. FIG. 5F illustrates the manner in which the circuit segments in FIGS. 5A through 5E are arranged for proper circuit interconnection. In the preferred embodiment, the circuit segments shown in FIGS. 5A through 5C are placed on a single circuit board termed a "processor board". The circuit segments shown in FIGS. 5D and 5E are placed on a second circuit board termed an "expansion board". The processor and expansion circuit boards are connected together with the connectors shown in FIGS. 5B and 5E. Hereinafter, FIGS. 5A through 5E are collectively referred to as "FIG. 5".

Figure 6A:
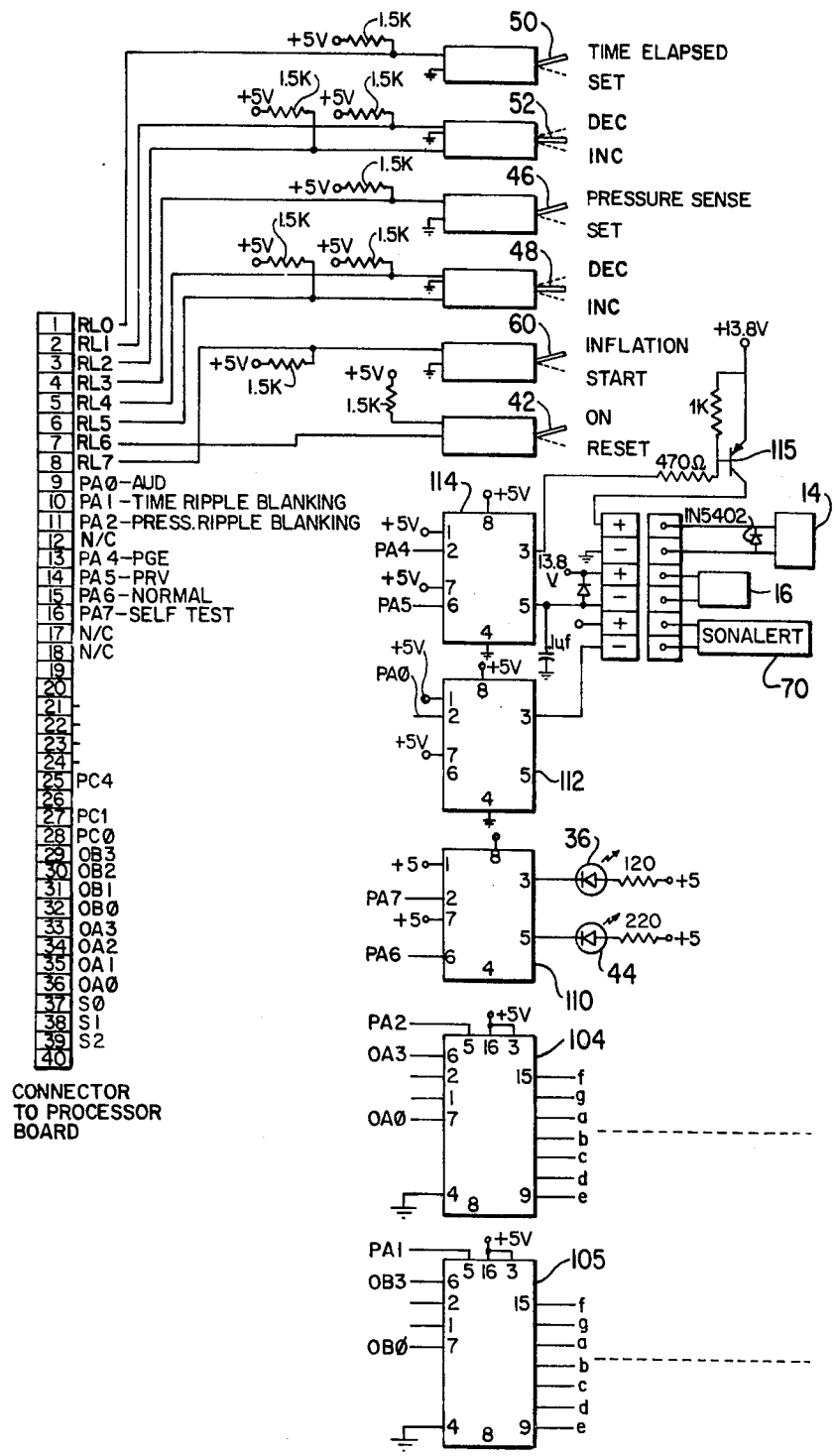

The control/display circuitry is shown in two separate FIGS. 6A and 6B. FIG. 6C illustrates the manner in which the circuit segments of FIGS. 6A and 6B are arranged for proper circuit interconnection. Hereinafter, FIGS. 6A and 6B are collectively referred to as "FIG. 6".

The microprocessor which regulates cuff pressure, drives the displays, etc. is an Intel 8085A microprocessor, shown at 78 in FIG. 5. Three Intel 2732 4K×8 bit electronically programmable read only memory ("EPROM") integrated circuits shown at 82A, 82B and 82C in FIG. 5 store the logic programs defining the sequence of operations by which microprocessor 78 controls the pneumatic tourniquet. An Intel 8155 integrated circuit ("I/O Device") shown at 80 in FIG. 5 provides 3 input/output ports and a timer. Although this integrated circuit has 256×8 bits of random access memory ("RAM"), this memory is not used. A 2K×8 bit RAM 81 comprising an Intel 4802 integrated circuit serves as a "scratchpad" memory in which volatile data is stored. EPROMs 82A through 82C are defined to contain memory addresses 0000 through 0FFF (hexadecimal), 1000 through 1FFF and 2000 through 2FFF respectively. RAM 81 is defined to contain memory addresses 4000 through 4FFF (note that since RAM 81 has only 2K capacity, each memory address location is repeated twice. For example, "4000" addresses the same memory location in RAM 81 as "4800").

A 30 line system bus 83 is used to pass information between microprocessor 78 and the other electronic devices with which it must communicate. Data and address information is passed in 8 bit multiplexed format on lines AD0 through AD7. Lines A0 to A11 are used to pass a 12 bit address in the range 0000 to 0FFF (hexadecimal). Lines A12 through A15 and the IO/M̄ line provide a further 5 bits of addressing information to two Intel 8205 memory select integrated circuits, 97 and 100. The IO/M̄ line activates memory select I.C. 97 if an input/output device is being addressed, and activates memory select I.C. 100 if a memory device is being addressed. By decoding the information presented on lines A12 through A15, memory select I.C. 97 is able to identify which of timer 86, I/O Device 80, analog to digital converter 84, switch and display interface 96, or serial communication interface 85 is to be addressed. In similar fashion, memory select I.C. 100 decodes the information on lines A12 through A15 to identify which of EPROMS 82A, 82B, 82C, or RAM 81 is to be addressed.

The input/output device addresses are defined as follows:

| | |
|---|---|
| ØX | I/O Device 80 |
| 1X | Switch and Display Interface 96 |
| 2X | Analog to Digital Converter 84 |
| 3X | Serial Communication Interface 85 |
| 4X | Timer Select (Timer 86) |
| 5X | Timer Gate (Timer 86) | where "X" denotes any value

The remaining 5 lines of system bus 83 carry timing information between microprocessor 78 and the other electronic devices with which it must communicate. The reset line provides a signal to reset all devices connected to system bus 83 whenever the power is turned on. The R̄D̄ line is used by microprocessor 78 to indicate that it expects to read data on lines ADØ through AD7, while the W̄R̄ line is used by microprocessor 78 to indicate that it is sending out data on lines ADØ through AD7. The ALE line provides a signal to indicate whether lines ADØ through AD7 are carrying address information or data.

A 6.144 MHz quartz crystal oscillator 116 (FIG. 5) serves as the master clock for microprocessor 78. The clock frequency is halved by microprocessor 78 to provide a 3.072 MHz signal at the "CLK" output of microprocessor 78 which is in turn presented to I/O Device 80. An internal timer provided on I/O Device 80 divides the "CLK" signal frequency by five to produce a 614.4 KHz signal which is in turn presented to analog to digital converter 84 and to timer 86. (The CLK frequency is divided because the integrated circuit timer used in the preferred embodiment is only able to handle signal frequencies of less than 2 MHz). Timer 86 (an 8253 integrated circuit) produces a 50 Hz output signal which is connected to the interrupt line of microprocessor 78. Thus, the operation of microprocessor 78 is "interrupted" at a 50 Hertz rate. The action taken by microprocessor 78 upon occurrence of each interrupt is hereinafter discussed under the heading "software". Timer 86 also produces a 4800 Hertz output signal which is used to clock Intel 8251 serial communication interface 85 (FIG. 5) at 300 baud. Serial communication interface 85 receives information in serial format from blood pressure sensing means 15 and re-assembles that information in 8 bit parallel format for transmission to microprocessor 78 on lines ADØ through AD7. Serial communication interface 85 also receives information from microprocessor 78 which it assembles into serial format for transmission to printer 27.

Address latch 98 (which is an Intel 8212 8 bit latch integrated circuit) demultiplexes the address information on lines ADØ through AD7 for presentation to system bus 83 on lines AØ through A7. This information is required by EPROMS 82A, 82B, 82C and RAM 81, since these devices require non-multiplexed address and data information.

The scaled 0-5 volt output of pressure transducer 88 is presented to analog to digital converter 84 at its input terminal IN0. Microprocessor 78 is programmed as hereinafter described to apply appropriate signals at the "start" and "ALE" terminals of analog to digital converter 84 to cause it to convert the pressure transducer output signal from analog to digital form. The 8 bit digital result is passed from analog to digital converter 84 on lines AD0-AD7. Signals generated by front panel switches 42, 46, 48, 50, 52 and 60 are passed from the control/display circuitry (FIG. 6) to switch and display interface 96 on lines RL0 through RL7 as follows:

| LINE | SIGNAL |
| --- | --- |
| RL0 | Switch 50 |
|  | Time "elapsed" or "set" |
| RL1 | Switch 52 |
| RL2 | Time "increase" or "decrease" |
|  | (2 bits) |
| RL3 | Switch 46 |
|  | Pressure "sensed" or "set" |
| RL4 | Switch 48 |
| RL5 | Pressure "increase" or |
|  | "decrease" (2 bits) |
| RL6 | Switch 42 |
|  | "on" or "reset" |
| RL7 | Switch 60 |
|  | "inflation start" |

I/O Device 80 generates signals for triggering the various alarms, activating pressurizing means 14, pressure relief means 16 and the front panel indicator lights, and also reads in information from switches 30 and 34 and from the power supply. These signals are conveyed as follows on lines PA0-PA7, PB0-PB1 and PC0-PC4:

| OUTPUT SIGNALS FROM I/O DEVICE 80 | SIGNAL |
| --- | --- |
| PA0 | audible alarm trigger |
| PA1 | time display ripple blanking |
| PA2 | pressure display ripple blanking |
| PA3 | not used |
| PA4 | activation signal for pressurizing means 14 |
| PA5 | activation signal for pressurizing relief means 16 |
| PA6 | activation signal for "normal" mode indicator light 44 |
| PA7 | activation signal for "self test" mode indicator light 36 |
| PB0 | activation signal for "adaptive" mode indicator light 32 |
| PB1 | activation signal for "constant" mode indicator light 33 |

| INPUT SIGNALS TO I/O DEVICE 80 | SIGNAL |
| --- | --- |
| PC0 | AC power fail alarm signal |
| PC1 | low battery power alarm signal |
| PC2 | "adaptive" position indicator for switch 30 |
| PC3 | "constant" position indicator for switch 30 |
| PC4 | "on arm" or "on leg" position indicator for switch 34 |

The audible alarm trigger signal appearing on line PA0 of I/O Device 80 is coupled to audible alarm 70 via National Semiconductor 75451 peripheral interface driver 112 as shown in FIG. 6. Audible alarm 70 is a SONALERT TM single tone audio alarm.

The activation signals for pressurizing means 14 and pressure relief means 16 which appear on lines PA4 and PA5 respectively of I/O Device 80 are coupled to another 75451 peripheral interface driver 114 as shown in FIG. 6. The activation signal on line PA4 is used to turn on drive transistor 115 which, in turn, couples a 13.8 volt drive signal to pressurizing means 14. Transistor 115 is an MJ2955 in the preferred embodiment.

The "normal" or "self test" mode status signals appearing on lines PA6 and PA7 respectively of I/O Device 80 are coupled to indicator lights 44 and 36 respectively via another 75451 peripheral interface driver 110 as shown in FIG. 6.

Switch and display Interface 96 is an Intel 8279 display/keyboard interface controller integrated circuit which reads the status of the switches on user control panel 26 and also handles the formatting of information appearing in displays 38 and 40. Microprocessor 78 converts the "pressure" or "time" information to be displayed into a BCD format which is passed to switch and display interface 96. The BCD digits representing "pressure" are then passed on lines OA0 through OA3 from switch and display interface 96 to a National Semiconductor DS8858 BCD to 7 segment decoder/driver 104 (FIG. 6), which passes the decoded 7 segment information to display 38. The BCD digits representing "time" are passed in similar fashion on lines OB0 through OB3 from switch and display interface 96 to display 40 via a second decoder/driver 105. Switch and display interface 96 also generates an appropriate 3 bit signal on lines S0 through S2 to determine which of the six individual display digits of displays 38 and 40 are to be activated. The S0-S2 signals pass through a National Semiconducter DS8863 hex inverting buffer 106 (FIG. 6) which absorbs sink current from the displays. As mentioned above, the "time" or "pressure" displays are caused to flash on and off when a pressure or time alarm is triggered. This is done by using the signals on lines PA1 and PA2 to trigger the "ripple blanking" function of decoder/drivers 104 and 105. This function causes the displays to go blank if they are displaying a value of zero. Flashing is achieved by having microprocessor 78 send zeros to switch and display interface 96 at regular intervals, while activating the PA1 or PA2 lines.

IV. Software

Appendix "A" to this specification is a source code listing for a computer program developed for the preferred embodiment. The computer program is written in the "C" programming language. Although it is believed that the computer program listing, together with the comments embedded therein, should enable those skilled in the art to understand the operation of the computer program, a brief overview of the operation of the computer program is now provided.

Execution of the computer program begins with the routine named "_main". The "_main" routine calls a subroutine named "initialize" which initializes the variables and timers used by the computer program and which also resets the I/O ports to prepare them to perform their specific input or output functions. The "_main" routine then queues a startup message for printing on printer 27 and then enters the self-test mode of operation. In the self-test mode displays 38 and 40 are caused to flash the numerals "888", audible alarm 70 is turned on and self-test indicator light 36 is illuminated. While in the self-test mode, the "_main" routine continually monitors reset switch 42. When reset switch 42 is depressed to the "reset" position, the self-test mode is terminated by turning off audible alarm 70, displaying the initial cuff pressure in display 38 and the numeral "0" in display 40, extinguishing indicator light 36 and flashing normal mode indicator light 44. The "_main" routine then waits for the operator to depress switch 60 to the "start" position. When that happens, the "control" routine is called.

The "control" routine has no end point. It continually samples the pressure in cuff 10. If that pressure is too low (i.e. more than 4 mmHg below the lower cuff pressure limit) then the "control" routine calls the "pump" subroutine which continues to monitor the pressure in cuff 10 while activating pressurizing means 14 until the cuff pressure has been raised to an acceptable value. If the pressure in cuff 10 is too high (i.e. more than 4 mmHg above the upper cuff pressure limit) then the "control" routine calls the "valve" subroutine which continues to monitor the pressure in cuff 10 while activating pressure relief means 16 until the pressure in cuff 10 decreases to an acceptable value. If the pressure in cuff 10 has remained within the cuff pressure limits for 15 seconds (i.e. if there has been no need to call either the "pump" or "valve" subroutines) then the "control" routine calls the "kinkcheck" subroutine which checks the integrity of the pneumatic system comprising cuff 10, tubing 12 and 20, pressurizing means 14, pressure relief means 16, and pressure sensing means 18. This is accomplished by activating pressurizing means 14 to cause a slight increase of the pressure in cuff 10 and then checking pressure sensing means 18 for an appropriately increased pressure reading. If no appropriately increased reading is obtained then the cuff pressure alarm is triggered and an error message is printed to notify the operator that he should check for kinks or obstructions in tubing 12 and 20 or for other problems with the pneumatic system.

The "pump" routine monitors the rate at which the pressure in cuff 10 is increased. If the cuff pressure exceeds 30 mmHg and if that pressure is not increasing at a satisfactory rate, then the "pump" subroutine calls the "kinkcheck" subroutine which, as indicated above, will check the integrity of the pneumatic circuit. In such cases however control is returned to the "pump" subroutine so that it may attempt to maintain the desired pressure in cuff 10 regardless of any problem with the pneumatic circuit. Because a "kinkcheck" cannot be reliably performed at cuff pressures below about 30 mmHg, the "pump" subroutine merely ensures that the pressure in cuff 10 is increased above 30 mmHg within a few seconds in preparation for a call to the "kinkcheck" subroutine.

If the "valve" subroutine determines that the pressure in cuff 10 is not within acceptable limits then it ensures that pressure relief means 16 remains deactivated (to avoid deflation of cuff 10) until the problem is resolved. Ordinarily, the "valve" subroutine calls the "v_kinkcheck" subroutine, which operates identically to the "kinkcheck" subroutine except that a slight pressure decrease (instead of a slight pressure increase) is used. However, if the "v_kinkcheck" subroutine determines that there is a problem with the integrity of the pneumatic system then the "kinkcheck" subroutine is repeatedly called to determine when the problem has been corrected. Thus the "kinkcheck" subroutine, rather than the "v_kinkcheck" subroutine, is called to avoid any further loss of cuff pressure. Only when both of these subroutines are satisfied with the integrity of the pneumatic system does cuff deflation continue.

Execution of the "control" routine is interrupted at the rate of 50 times per second. The interrupt frequency is determined by the real time clock on timer 86. Upon occurrence of an interrupt, control is transferred to the "rst75" subroutine which increments the various timer variables used by the computer program, checks whether blood pressure sensing means 15 has transmitted a data character over serial communication interface 85, calls the "adapti" subroutine to determine whether or not a new value of the patient's systolic blood pressure has been determined by blood pressure sensing means 15, transmits the next data character of any messages which are waiting to be printed on printer 27, examines the various switches to determine whether or not the operator wishes to intervene in the operation of the pneumatic tourniquet and updates the various displays and alarm indicators as operational conditions require.

The various subroutines activated when an interrupt causes control to be transferred to the "rst75" routine will not be discussed. These subroutines are not all necessarily executed each time an interrupt occurs. This is to ensure that precedence is given to the "control" routine which monitors the pressure in cuff 10. The subroutine sequence activated by the "rst75" subroutine must not take more than 1/50th second or else no time would be left for execution of the "control" routine.

The "frontpanel" subroutine monitors the status of switches 42, 46, 48, 50 and 52 and takes appropriate action to enable the operator to select the pressure to which cuff 10 is to be initially pressurized and the cuff pressurization time period. The "frontpanel" subroutine also monitors the AC power fail alarm and low battery power alarm signals on lines PC0 and PC1 of I/O Device 80. If either alarm is triggered appropriate action is taken as previously decribed.

The "alm_check" subroutine activates audible alarm 70 upon occurrence of an alarm and, while the alarm condition continues, updates the information in displays 38 and 40, and causes those displays to flash as alarm conditions dictate. Once activated, audible alarm 70 is not silenced unless the conditions which activated the alarm are corrected. Audible alarm 70 may however be temporarily silenced for 30 seconds by depressing switch 42 to the "reset" position. However, if a new alarm is generated during the temporary 30 second silencing interval, audible alarm 70 is immediately reactivated.

The "sense" subroutine initiates operation of analog to digital converter 84 and then causes the result of an analog to digital conversion to be read and stored. The value returned by the "sense" subroutine is an average of the latest analog to digital conversion and the two immediately preceeding analog to digital conversions. Averaging is used to filter and reduce the effect of any extraneous electrical interference.

The "divide" subroutine performs mathematical divisional operations necessary to convert numbers into binary coded decimal format for printing or display purposes.

The "dis_pres" and "dis_time" subroutines respectively cause displays 38 and 40 to display the current values of pressure in cuff 10 or the time elapsed since cuff 10 was first pressurized.

The "bit" subroutine assigns values to individual bits in a bit field structure.

The "devout" subroutine is used to activate devices such as pressurizing means 14 by passing appropriate commands to those devices.

The "delay" subroutine simply waits for an interval of time represented by the argument value passed to the subroutine.

The "serial" subroutine handles the input and output of data via serial communication interface 85.

The "dina_store" and "tk_store" subroutines store characters received from blood pressure sensing means 15, pressure sensing means 18, or microprocessor 22, in preparation for subsequent output of a character string to printer 27 by the "print_msg" subroutine.

The "num_store" subroutine converts numerical data into BCD and then ASCII format, and then constructs a character string by calling the "tk_store" subroutine.

The "que" subroutine manages a reusable data area in cyclical fashion by allocating available data space upon demand by the various other subroutines. The "d_que" subroutine performs a reciprocal function by releasing previously allocated data space when it is relenquished by the various subroutines.

The "print_msg" subroutine checks to see if there have been any changes in the operational mode of the pneumatic tourniquet, in the setting of any of the front-panel switches, or in the status of any alarms. If any such changes have occurred then appropriate messages are assembled and printed on printer 27. The character strings from which the messages are assembled are defined in the "initialize" routine.

The "elapse" subroutine is periodically activated to print on printer 27 the current elapsed time displayed in elapsed time display 40.

The "adapti" subroutine handles all procedures required to set the pressure in cuff 10 "adaptively" in response to the blood pressure output signal produced by blood pressure sensing means 15. The "adapti" subroutine also monitors the status of switch 30 and causes corresponding changes in the operational mode of the pneumatic tourniquet.

In the "adaptive" mode the "adapti" subroutine reads the data stream produced by blood pressure sensing means 15 and analyzes that data to determine whether or not blood pressure sensing means 15 has made an appropriate measurement of the patient's systolic blood pressure. If an appropriate measurement has been made it is checked to ensure that it is within acceptable limits (i.e. between 80 mmHg and 160 mmHg). A measurement outside acceptable limits causes production of the blood pressure alarm signal to trigger the blood pressure alarm. The measurement is also compared to the immediately preceding measurement obtained from blood pressure sensing means 15 to ensure that the absolute value of the difference between those measurements does not exceed a selected amount (which, in the preferred embodiment, is about 32 mmHg). A difference between successive measurements of more than 32 mmHg causes production of the blood pressure fluctuation alarm signal to trigger the blood pressure fluctuation alarm. If neither alarm is triggered then the pressure in cuff 10 is set at the average of the three blood pressure measurements most recently obtained from blood pressure sensing means 15 plus a safety margin of either 90 mmHg (if cuff 10 is applied to an arm) or 125 mmHg (if cuff 10 is applied to a leg). If the "adapti" subroutine does not receive a new blood pressure value from blood pressure sensing means 15 once every 3 minutes, then the inhibit alarm signal is produced to trigger the inhibit alarm.

If the pneumatic tourniquet is operating in the "constant" mode then the "adapti" subroutine sets the pressure in cuff 10 to the pressure pre-selected by the operator.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

APPENDIX "A"

```
/******************************************************************/
/*      MAIN.AT2     *                                            */
/****************             * MARK 2 *                          */
/*                                                                */
/*   THE ROUTINE: _main()                                         */
/*                ---------                                       */
/*   This is the entry point for the "C" tourniquet program.      */
/*                                                                */
/*   -all constants                                               */
/*   -all globals                                                 */
/*   -all subprograms are declared in this block.                 */
/*                                                                */
/*                                                                */
/*        THIS ROUTINE CALLS: initialize, dis_time, dis_pres, control, */
/*                            devout                              */
/*                                                                */
/*        GLOBALS: see below                                      */
/*                                                                */
/*        STATIC LOCALS: n/a                                      */
/*                                                                */
/*        AUTOMATIC LOCALS: n/a                                   */
/*                                                                */
/*        ARGUMENTS: none                                         */
/*                                                                */
/*        CONSTANTS: all constants defined in this file           */
/*                                                                */
/*                                                                */
/******************************************************************/
```

```c
/* to vary TK for use between arm & leg change: P_START, DIN_MARG, and */
/*                                               SCALE                 */ include "DY0:STD.H"

/* CONSTANTS:                                                          */
/* Port definitions:                                                   */ define FPIN 0x10           /* frontpanel switches */
define FPOUT 0x01          /* devices controlled by frontpanel ie pump etc.*/
define STATIN 0x03         /* power status */ define ALPORT 0x03         /* arm/leg selector port */
define ALBIT 0x10          /* arm/leg selector bit */ define DISP 0x10           /* BCD displays */ define A_D 0x20            /* A/D converter */ define S_DATA 0x30         /* serial port data location */
define S_STATUS 0x31       /* serial port status location */ define DINALED 0x02        /* adaptive / constant LED port */
define P_MODE 0x00         /* 8155 control port */
#define P_SETUP 0xc3        /* 8155 setup byte - PA=output, PB=output, */
                            /* PC=input, & start timer                 */
#define P_T1 0x04           /* 8155 timer port */
define P_T2 0x05 define P_T1SET 0x05        /* set 8155 timer to square wave & divide by 5 */
define P_T2SET 0x40 define DK_MODE 0x11        /* display/keyboard mode control port      */
define DK_SETUP 0x05       /* left entry decoded scan sensor matrix   */
#define DK_T 0x3f           /* 8279 timer divide by 31                 */
#define DK_READ 0x40        /* read sensor row 0 - no auto increment   */
#define DK_BLANK 0xdf       /* use "f" to blank display                */
#define DK_IA 0xa8          /* inhibit nibble A                        */
#define DK_IB 0xa4          /* inhibit nibble B                        */
define DK_WRITE 0x90       /* write loc 0 w/ auto increment           */ define T_MODE 0x43         /* timer mode control port */ define T_SET0 0x36         /* timer modes */
define T_SET1 0x72
define T_SET2 0xb6 define T_0 0x40            /* timer counters - square wave */
define T_1 0x41            /*                  oneshot     */
#define T_2 0x42            /*                  square wave */

/* timer count lengths (must be less than 32767) */
#define T_PG0 12288         /* RST7.5 interrupt clock */
#define T_PG1 0             /* not used at present    */
define T_PG2 128           /* 300X16 clock for uart  */ define T_GO 0x50           /* port addr used to start the timers */ define S_MODE 0x4e         /* 1 stop bit, no parity, 8 data bits, clk 16X baud */
define S_CONTROL 0x37      /* RTS*, DTR*, enable reciever, enable transmitter  */
#define S_ERROR 0x38        /* serial recieved data error mask */
#define SR_DATA 0x02        /* serial data recieved mask */
#define ST_DATA 0x01        /* serial data transmitted mask */

/* logical definitions: */ define HIGH 1
```

```
#define LOW 0
#define ON 1
#define OFF 0
#define YES 1
#define NO 0
/* initialization values: */ define T_START 60      /* default timer setting = 60 min. */

/* limits: */ define P_MAX 400       /* max inflation = 400mmHg */
define P_MIN 30        /* min inflation = 30mmHg */
#define T_MAX 180       /* max allowed timer setting = 180 min. */
#define LIMIT 4         /* control hysterisis */

/* timing constants: */
define CLK 2           /* rst75 period (10ms) */ define TIME0 6000      /* 10ms per minute */
define TIME1 2         /* 10ms  interval between checking serial port */
#define TIME2 10        /* 10ms  interval between checking frontpanel */
define TIME3 50        /* 10ms  1/2 display flash period */ define AUDIO_OFF 300   /* 1/10s  audible mute time */ define SLOW_COUNT 25   /* 1/10s  length of slow count when setting P or T */ define LOW_TIME 750    /* 10ms  time allowed for pressure to rise above 30mHg */ define KC_TIME 1500    /* 10ms  interval between checking for kinks */ define PC_TIME 25      /* 10ms  interval between pressure checks when P is OK */ define PRES1       0x0001  /* used as masks in manipulating struc bits */
define PRES2       0x0002
#define PRES3       0x0004
#define TIME        0x0008
#define POWERFAIL   0x0010
#define LOW_BATT    0x0020
#define DINA1       0x0040
#define DINA2       0x0080
#define DINA3       0x0100
define DINA4       0x0200 define TSET        0x0001
define TDEC        0x0002
#define TINC        0x0004
#define PSET        0x0008
#define PDEC        0x0010
#define PINC        0x0020
#define ALM_RESET   0x0040
#define INFL_STRT   0x0080
#define ADAPT       0x0100
define CONST       0x0200 define HORN        0x0001
define T_RIPPLE    0x0002
#define P_RIPPLE    0x0004
/* */
#define PUMP        0x0010
#define VALVE       0x0020
#define NORM        0x0040
define SLF_TST     0x0080 define SPOWERFAIL  0x0001
define SLOW_BATT   0x0002
```

```
/* constants pertaining to arm operations are preceded by an "A", and  */
/* those for leg by an "L" */ define ASCALE 1      /* the Kc_on[] & v_Kc_on[] times are multiplied by */
define LSCALE 2      /* this scale factor. it is typically =1 for arm   */
                      /* tourniquets and 2 for leg tourniquets           */ define AP_START 200  /* default initial inflation */
define LP_START 275 define ADIN_MARG 90  /* margin between systolic & cuff P in adapt mode */
define LDIN_MARG 125

/* variables to complement above arm/leg constants above */ unsigned short p_start=0,din_marg=0,scale=0;

unsigned char armleg=0;    /* high means arm operation / low means leg */ unsigned short m10=0, m100=0, m1000=0;             /* timing counters */
unsigned short  milli_sec=0, timer1=0, timer2=0;
unsigned short minutes=0, pressure=0;     /* elapsed time, sensed P */
unsigned short t_set=0, t_setting=0, p_set=0, p_setting=0;
                                        /* the set time, pressure */
unsigned short Kc_on[8]=0, v_Kc_on[8]=0;/*Kinkcheck pressure dependant */
                                        /* pump, valve on times       */
unsigned char pulse=0, tick=0, self_test=0;          /* all logical */
        /* "pulse" occurs if a rst75 occurs, "tick" is a sq wave, */
                   /* "self_test" is true if in selftest mode */
unsigned short *pt_alm=0,*pt_o_alm=0,*pt_d_alm=0;/*ptrs to structs use */
unsigned short *pt_swtch = 0, *pt_o_swtch = 0;     /* when referencing */
unsigned short *pt_device = 0, *pt_stat = 0;  /*whole struct as a unit */
unsigned short *pt_dina = 0;

/* static variables used locally, necessary in case 8080 C statics   */
/*   don't work right                                                */ unsigned short sw_slow = 0;                   /* used in front_panel */
unsigned short sona_hold = 0;                 /* used in alm_check   */
unsigned short p1 = 0, p2 = 0, p3 = 0;        /* used in sense       */

/* variables used in the control of the buffers and ques for the    */
/* printer                                                          */ define BUFFER 600                          /* size of dinamap buffer */
unsigned char dina_buff[BUFFER+1] =0;                /* dinamap buffer */
unsigned char *din_string =0;   /* pointer to string being assembled  */
unsigned short dina_ptr =0;     /* subscript pointer to next char loc */ define TK_BUFFER 50   /* size of TK variable buffer */
unsigned char tk_buff[TK_BUFFER+1] =0; /* TK buffer for vars like nums */
unsigned char *tk_string =0; /* pointer to string being assembled     */
unsigned short tk_ptr =0;      /* subscript pointer to next TK char loc */ define Q_BUFFER 50   /* size of the que of pointers to strings of text*/
char *que_buff[Q_BUFFER] =0;    /* que of pointers                    */
unsigned short que_ptr =0, d_que_ptr =0;   /* subscript pointers to next*/
          /* locations of pointers to store and fetch respectively */ define DINA_TIME 50/* # intrpts used by TK to detect end of DINA strg */
unsigned short nodata =0; /* used to det. if end of dina string reached*/
unsigned char c_buff[5] =0;  /* buffer to hold last 5 chars from dina */
unsigned char *pointer =0; /* pointer to next char to be printed      */
unsigned char mdl_ptr =0;  /* logical to rem if prts in middle of strng*/
```

```c
#define NULL 20              /* the number of nulls to insert after a CR */
unsigned short null_cnt =0;  /* used in serial to count nulls output    */

/* variables required for tourniquet message printing system           */
unsigned short old_pset=0, old_tset=0;/* detect when p_set or t_set chg*/
unsigned char old_adaptive=0; /*detect change in constant/adaptive mode*/

/* pointers to text strings in rom [ defined in initialize() ]         */
unsigned char *msg1=0,*msg2=0,*msg3=0,*msg4=0,*msg5=0,*msg6=0,*msg7=0;
unsigned char *msg8=0,*msg9=0,*msg10=0,*msg11=0,*msg12=0,*msg13=0;
unsigned char *msg14=0,*msg15=0,*msg16=0,*msg17=0,*msg18=0,*msg19=0;
unsigned char *msg20=0,*msg21=0,*msg22=0,*msg23=0,*msg24=0,*msg25=0;
unsigned char *msg26=0,*msg27=0,*msg28=0,*msg29=0,*msg30=0;

/* constants / variables needed for the adaptive procedures            */ define DIN_MIN  80          /* minimum allowed readings from DINAMAP  */
define DIN_MAX  160         /* maximum allowed readings from DINAMAP  */
#define DIN_TIME 4           /* max # of minutes between valid readings */
#define DIN_DIF  32          /* max difference between succesive readngs*/
unsigned char adaptive=0;    /* used as a logical to monitor TK mode   */ short p_adapt=0,rd_minute=0,p_ad[3]=0; /* used as statics in adapti()  */
unsigned char strt_adapt=NO; /* logical - used to tell first adapt read*/ define ADAPTLED    0x0001   /* used as masks for bit structures       */
define CONSTLED    0x0002

/* bit field structures for adaptive procedures */ struct begin
        unsigned adaptled    :1;  /* used for adaptive / constant LED's */
        unsigned constled    :1;
        end dina=0;

/* bit field structures: */
struct begin
        unsigned pres1       :1;
        unsigned pres2       :1;
        unsigned pres3       :1;
        unsigned time        :1;
        unsigned powerfail   :1;
        unsigned low_batt    :1;
        unsigned dina1       :1;
        unsigned dina2       :1;
        unsigned dina3       :1;
        unsigned dina4       :1;
        end alm=0, old_alm=0, dina_alm=0;

struct begin
        unsigned tset        :1;
        unsigned tdec        :1;
        unsigned tinc        :1;
        unsigned pset        :1;
        unsigned pdec        :1;
        unsigned pinc        :1;
        unsigned alm_reset   :1;
        unsigned infl_strt   :1;
        unsigned adapt       :1;
        unsigned const       :1;
        end swtch=0, old_swtch=0;
```

```
struct begin
        unsigned horn         :1;
        unsigned t_ripple     :1;
        unsigned p_ripple     :1;
        unsigned              :1;
        unsigned pump         :1;
        unsigned valve        :1;
        unsigned norm         :1;
        unsigned slf_tst      :1;
        end device=0;

struct begin
        unsigned spowerfail   :1;
        unsigned slow_batt    :1;
        unsigned              :1;
        unsigned              :1;
        end stat=0;

#include "DY1:INIT.AT2"
#include "DY1:CNTRL.T2K"
#include "DY1:RST75.AT2"
#include "DY1:FRONTP.AT2"
#include "DY1:ALMCK.AT2"
#include "DY1:PUMP.T2K"
#include "DY1:VALVE.T2K"
#include "DY1:KINKCK.T2K"
#include "DY1:VKNKCK.T2K"
#include "DY1:SENSE.T2K"
#include "DY1:DIVIDE.T2K"
#include "DY1:DISPRS.T2K"
#include "DY1:DISTIM.T2K"
#include "DY1:BIT.T2K"
#include "DY1:DEVOUT.T2K"
#include "DY1:DELAY.T2K"
#include "DY1:SERIAL.AT2"
#include "DY1:TRAP.T2K"

#include "DY1:DINSTR.AT2"
#include "DY1:TKSTR.AT2"
#include "DY1:NUMSTR.AT2"
#include "DY1:QUE.AT2"
#include "DY1:DQUE.AT2"
#include "DY1:PRTMSG.AT2"
#include "DY1:ELAPSE.AT2"
#include "DY1:ADAPTI.AT2"
_main()
begin
    initialize();

que("\n      ADAPTIVE ELECTRONIC TOURNIQUET\n\nVerify that displays are ");
    que("flashing '888' and\nthat audible alarm is on.\n\npress ALARM RESET");
    que("\nPressure and time limit may now be set.\n\npress INFLATION START");
    que(" when ready\n\npress ADAPTIVE for dynamic pres. control\n\n");

if (armleg) then que("ARM");
                else que("LEG");
    que(" operation\n\n\n\n\n");

self_test = ON;     /* used to inhibit alarm checks & display updates */
    pressure = 888;                   /* set up variables for self test */
    bit(pt_device,SLF_TST,ON);
    bit(pt_device,HORN,ON);
    devout();

while (!((in(FPIN))&ALM_RESET)) minutes = 888;   /* wait "ALARM RESET"*/ pressure = 0;
    minutes = 0;
    self_test = OFF;
    bit(pt_device,SLF_TST,OFF);
    bit(pt_device,HORN,OFF);
    devout();
```

```
    while (!swtch.infl_strt) /* wait for "INFLATION START" to be pressed */
        begin
        minutes = 0;

if (tick) then bit(pt_device,NORM,ON); /* flash the NORMAL light */
                 else bit(pt_device,NORM,OFF); /* in pre-inflation mode */
        devout();

pressure = sense(); /* display pressure for calibration purposes */
        end bit(pt_device,NORM,ON);
    devout();
    minutes = 0;
    milli_sec = 0;
    control();                    /* control never returns, but regulates P */
end /***********************************************************************/
/*    INIT.AT2    *                                                    */
/*****************                                                     */
/*                                                                     */
/*    THE ROUTINE: initialize()                                        */
/*    ---------------                                                  */
/*    This routine is executed following a hardware restart to initialize */
/*    the device port, the hardware timers, and certain variables.    */
/*                                                                     */
/*                                                                     */
/*        THIS ROUTINE CALLS: devout                                   */
/*                                                                     */
/*        GLOBALS: STR alm, old_alm, swtch, old_swtch, stat, device   */
/*                 US m10, m100, m1000, minutes, pressure              */
/*                    Kc_on[], v_Kc_on[], p_set, p_setting             */
/*                 US milli_sec, timer1, timer2                        */
/*                 UC tick, pulse, self_test                           */
/*                                                                     */
/*        STATIC LOCALS: none                                          */
/*                                                                     */
/*        AUTOMATIC LOCALS: none                                       */
/*                                                                     */
/*        ARGUMENTS: none                                              */
/*                                                                     */
/*        CONSTANTS: OFF, T_START, P_START, FPOUT, T_MODE, T_0, T_1, T_2 */
/*                   T_SET0, T_SET1, T_SET2, T_PG0, T_PG1, T_PG2, P_T1, */
/*                   P_T2, P_T1SET, P_T2SET, P_MODE, P_SETUP, DK_MODE,  */
/*                   DK_T, DK_SETUP, DK_READ, DK_BLANK                 */
/*                                                                     */
/*                                                                     */
/***********************************************************************/ initialize()

begin

/* initialization for printer - done first before needed by interrupts */ nodata = DINA_TIME + 1; /* ensure tk thinks it isn't in a dina strng*/
    dina_ptr = tk_ptr = que_ptr = d_que_ptr = null_cnt = 0;
    mdl_ptr = LOW;

pt_alm = &alm;              /* intialize the pointers to the structures */
    pt_o_alm = &old_alm;
    pt_d_alm = &dina_alm;
    pt_swtch = &swtch;
    pt_o_swtch = &old_swtch;
    pt_device = &device;
    pt_stat = &stat;
    pt_dina = &dina;
```

```
out(P_T2,P_T2SET);                          /* set up 8155 timer */
out(P_T1,P_T1SET);
out(P_MODE,P_SETUP);                        /* set up 8155 parallel ports */

*pt_device = 0;                             /* turn off all devices */
devout();

out(DK_MODE,DK_SETUP);      /* set up keyboard/display controller */
out(DK_MODE,DK_T);
out(DK_MODE,DK_READ);
out(DK_MODE,DK_BLANK);

out(T_MODE,T_SET0);                         /* setup timer modes */
out(T_MODE,T_SET1);
out(T_MODE,T_SET2);

out(T_0,T_PG0 & 0x00ff);                    /* program timers */
out(T_0,((T_PG0 & 0xff00) >> 8));
out(T_1,T_PG1 & 0x00ff);
out(T_1,((T_PG1 & 0xff00) >> 8));
out(T_2,T_PG2 & 0x00ff);
out(T_2,((T_PG2 & 0xff00) >> 8));

out(S_STATUS,S_MODE);                       /* set up serial ports */
out(S_STATUS,S_CONTROL);

in(T_GO);                                   /* restart the timers */

*pt_alm = *pt_o_alm = *pt_d_alm = 0;        /* initialize variables */
*pt_o_swtch = *pt_swtch = 0;

self_test = OFF;

armleg = in(ALPORT) & ALBIT;                /* read whether arm or leg mode */ if (armleg) then
    begin
        scale = ASCALE;                     /* arm operation */
        p_start = AP_START;
        din_marg = ADIN_MARG;
    end
  else
    begin
        scale = LSCALE;                     /* leg operation */
        p_start = LP_START;
        din_marg = LDIN_MARG;
    end m10 = m100 = m1000 = minutes = pressure = 0;
milli_sec = timer1 = timer2 = 0;
tick = pulse = 0;

t_set = t_setting = T_START;
p_set = p_setting = p_start;
    kc_on[0] = 4 * scale;     /* 10's of ms for the p range 0-63    mmHg  */
    kc_on[1] = 5 * scale;     /*                       64-127              */
    kc_on[2] = 6 * scale;     /*                       128-191             */
    kc_on[3] = 9 * scale;     /*                       192-255             */
    kc_on[4] = 11 * scale;    /*                       256-319             */
    kc_on[5] = 14 * scale;    /*                       320-383             */
    kc_on[6] = 16 * scale;    /*                       384-447             */
    kc_on[7] = 20 * scale;    /*                       448-511             */ v_kc_on[0] = 150 * scale; /* 10's of ms for the p range 0-63    mmHg  */
    v_kc_on[1] = 100 * scale; /*                       64-127              */
    v_kc_on[2] = 70 * scale;  /*                       128-191             */
    v_kc_on[3] = 35 * scale;  /*                       192-255             */
    v_kc_on[4] = 24 * scale;  /*                       256-319             */
    v_kc_on[5] = 16 * scale;  /*                       320-383             */
    v_kc_on[6] = 9 * scale;   /*                       384-447             */
    v_kc_on[7] = 2 * scale;   /*                       448-511             */
```

```
/* assignments concerned with the tourniquet message printing system    */ old_pset = p_set;
    old_tset = t_set;

/* message definitions */ mss1  = "<< ALARM RESET >>    ";
    mss2  = "<< INFLATION START >>    ";
    mss3  = ">>elapsed time =";
    mss4  = " minutes\n";
    mss5  = " mmHg\n";
    mss6  = "set pressure =";
    mss7  = "ADAPTIVE\n";
    mss8  = "CONSTANT\n";
    mss9  = ">> time limit changed from";
    mss10 = ">> set pressure changed from";
    mss11 = " to";
    mss12 = "\n\n\n\n\n";                              /* CR/LF 's */
    mss13 = "\033\013\033\013\033\013\033\013\015";    /* reverse LF 's + CR */ mss14 = "** insufficient rate of pressure ";
    mss15 = "    sensed pressure =";
    mss16 = "increase\n";
    mss17 = "decrease\n";
    mss18 = "** pressure less than";
    mss19 = "   LARGE LEAK";
    mss20 = "** maximum time limit exceeded\n";
    mss21 = "** AC power disconnected - running on BATTERY\n";
    mss22 = "** LOW BATTERY restore AC IMMEDIATELY\n";
    mss23 = ">>AC power restored ";
    mss24 = "** measured patient blood-pressure is not\n    between";
    mss25 = "** too long since last blood pressure reading\n";
    mss26 = "** DINAMAP in Kpascals - change to mmHg\n";
    mss27 = "** blood pressure change greater than";
    mss28 = ">> mode changed to ";
    mss29 = "**         CHECK for KINKs";
    mss30 = " or LEAKs\n";

/* adaptive initialization assignments */ old_adaptive = adaptive = OFF;
    strt_adapt = NO;
    bit(pt_dina,CONSTLED,ON);
    bit(pt_dina,ADAPTLED,OFF);
    out(DINALED,*pt_dina);

end
```

```
/****************************************************************/
/*    CNTRL.TK    *                                              */
/****************                                                */
/*                                                               */
/*   THE ROUTINE: control()                                      */
/*                ---------                                      */
/*   This routine periodically monitors the cuff pressure, and calls */
/*   "pump" or "valve" as required if the pressure strays outside of */
/*   the limits. This routine also periodically calls "kink_check" to */
/*   verify the integrity of the system, including the pneumatics. */
/*                                                               */
/*                                                               */
/*       THIS ROUTINE CALLS: sense, valve, pump, delay, kinkcheck */
/*                                                               */
/*       GLOBALS: STR alm                                        */
/*                US pressure, p_set                             */
/*                                                               */
/*       STATIC LOCALS: none                                     */
/*                                                               */
/*       AUTOMATIC LOCALS: none                                  */
/*                                                               */
/*       ARGUMENTS: none                                         */
/*                                                               */
/*       CONSTANTS: LIMIT, KC_TIME, PC_TIME                      */
/*                                                               */
/*                                                               */
/****************************************************************/ control()

begin timer1 = 0;                     /* initiate kinkcheck every KC_TIME ms */ while (1)
        begin pressure = sense();              /* measure the cuff pressure */ if ( pressure > (p_set + LIMIT) ) then
            begin                        /* the pressure is too high */
            valve();
            timer1 = 0;
            end else
            if ( pressure < (p_set - LIMIT) ) then
                begin                    /* the pressure is too low */
                pump();
                timer1 = 0;
                end
        delay(PC_TIME);   /* wait PC_TIME ms for pressure to stabilize */ if (alm.pres1||alm.pres2||alm.pres3||(timer1 >= KC_TIME)) then
            begin
            kinkcheck();      /* check for integrity of control system */
            timer1 = 0;
            end end
end
```

```
/***************************************************************/
/* RST75.AT2.                                                  */
/***************                                               */
/*                                                             */
/*    THE ROUTINE: rst75()                                     */
/*                 --------                                    */
/*                                                             */
/*    This routine is invoked by the hardware real time clock  */
/*    to: keep track of elapsed time, check condition of serial port, */
/*        update and check the frontpanel for switch closures, */
/*        update alarm indicators.                             */
/*                                                             */
/*        THIS ROUTINE CALLS: serial, dis_time, dis_pres, frontpanel, */
/*                            alm_check                        */
/*                                                             */
/*                                                             */
/*        GLOBALS: US m10, m100, m1000, minutes                */
/*                 US milli_sec, timer1, timer2                */
/*                 UC pulse, tick                              */
/*                 STR alm                                     */
/*                                                             */
/*        STATIC LOCALS: none                                  */
/*                                                             */
/*        AUTOMATIC LOCALS: none                               */
/*                                                             */
/*        ARGUMENTS: none                                      */
/*                                                             */
/*        CONSTANTS: CLK, TIME0, TIME1, TIME2, TIME3, HIGH, ON */
/*                                                             */
/*                                                             */
/*                                                             */
/***************************************************************/ rst75()
begin timer1 += CLK;                            /* used for loop timing */
    timer2 += CLK;                            /* used for DELAY timing */ milli_sec += CLK;
    if (milli_sec >= TIME0) then              /* time0 msec per minute */
        begin
        milli_sec = 0;
        ++minutes;
        end pulse = HIGH;    /* can be used by a foreground routine to determine */
                 /*                           when a clock has occurred */ m10 += CLK;
    if (m10 >= TIME1) then
        begin
        m10 = 0;

serial();                             /* check the serial port */
        adapti();                /* check for pressure input from DINAMAP */
        end if (m100 == 0) then print_msg();   /* que any TK messages (during a  */
    m100 += CLK;                       /* different interrupt than when  */
    if (m100 >= TIME2) then            /* the FP & alarms are serviced)  */
        begin
        m100 = 0;
        if ((minutes >= t_set) && !self_test) then bit(pt_alm,TIME,ON);
                /* time alarm (minutes set to "888" during self test) */
            else bit(pt_alm,TIME,OFF);

frontpanel();          /* check frontpanel switches and alarms */
        alm_check();           /* update alarm indicators with latest status */
                               /* and display current time and pressure */
        end
```

```
        m1000 += CLK;
        if (m1000 >= TIME3) then
            begin
            m1000 = 0;
            tick = HIGH - tick;                /* tick is a software square wave */
            end
end
/*******************************************************************************/
/*    FRONTP.AT2   *                                                           */
/******************                                                            */
/*                                                                             */
/*    THE ROUTINE: frontpanel()                                                */
/*                 ---------------                                             */
/*    This routine updates the frontpanel displays, and reads the              */
/*    frontpanel switches adjusting the appropriate parameter as required.     */
/*                                                                             */
/*                                                                             */
/*        THIS ROUTINE CALLS: dis_pres, dis_time                               */
/*                                                                             */
/*        GLOBALS: STR alm, stat, swtch, old_swtch                             */
/*                 US  t_set, p_set, p_setting                                 */
/*                                                                             */
/*        STATIC LOCALS: US sw_slow    - used to determine if a display        */
/*                                       being set should be changed           */
/*            (defined globally)        quickly or slowly.                     */
/*                                                                             */
/*                                                                             */
/*        AUTOMATIC LOCALS: none                                               */
/*                                                                             */
/*        ARGUMENTS: none                                                      */
/*                                                                             */
/*        CONSTANTS: STATIN, FPIN, SLOW_COUNT, P_MAX, P_MIN, T_MAX, OFF        */
/*                                                                             */
/*                                                                             */
/*******************************************************************************/ frontpanel()

begin
if (!self_test) then
 begin

*pt_stat = ( ~in(STATIN) ) & 0x03;
    bit(pt_alm,POWERFAIL,stat.spowerfail);          /* update power status */
    bit(pt_alm,LOW_BATT,stat.slow_batt);

*pt_o_swtch = *pt_swtch;   /* the ordering of these 2 stmts is imp. */
    *pt_swtch = in(FPIN);

*pt_swtch += ((unsigned short) (~in(STATIN))) & 0x0c) << 6;
                                        /* set current switch settings */ if (!swtch.pset && old_swtch.pset && !adaptive) then p_set=p_setting;
                                                        /* change to new p. */
    if (swtch.pset) then
        begin dis_pres(p_setting);
        bit(pt_device,P_RIPPLE,OFF);
    if (swtch.pinc || swtch.pdec) then        /* adjust set pressure */
        begin ++sw_slow;
        if (!old_swtch.pinc && !old_swtch.pdec) then sw_slow = 0;
        if ( (sw_slow >= SLOW_COUNT) || ( (sw_slow % 5) == 0 ) ) then
            begin
```

```
                if (swtch.pinc) then
                    begin
                    if (p_setting < P_MAX) then ++p_setting;
                    if (p_setting < P_MIN) then p_setting = P_MIN;
                    end else
                    begin
                    if (p_setting > P_MIN) then --p_setting;
                      else p_setting = 0;                    /* deflate cuff */
                    end end
          end
      end if (!swtch.tset && old_swtch.tset) then t_set = t_setting;

if (swtch.tset) then
    begin dis_time(t_setting);
    bit(pt_device,T_RIPPLE,OFF);

if (swtch.tinc || swtch.tdec) then      /* adjust max time limit */
        begin ++sw_slow;
        if (!old_swtch.tinc && !old_swtch.tdec) then sw_slow = 0;

if ( (sw_slow >= SLOW_COUNT) || ( (sw_slow % 5) == 0 ) ) then
            begin if (swtch.tinc) then
                begin
                if (t_setting < T_MAX) then ++t_setting;
                end else
                begin
                if (t_setting > 0) then --t_setting;
                end end
        end
    end
```

```
/***************************************************************************/
/*    ALMCK.AT2   *                                                        */
/*****************                                                         */
/*                                                                         */
/*    THE ROUTINE: alm_check()                                             */
/*                ------------                                             */
/*                                                                         */
/*    This routine updates the time and pressure displays, and indicates   */
/*    to the operator if any alarm conditions are present. The operator    */
/*    may silence the audible alarm for AUDIO_OFF tenths of a second by    */
/*    pressing the "ALARM RESET" switch. The audible alarm is sounded      */
/*    for all alarm conditions.                                            */
/*                                                                         */
/*                                                                         */
/*       THIS ROUTINE CALLS: dis_pres, dis_time, devout                    */
/*                                                                         */
/*       GLOBALS: STR swtch, old_swtch, alm, old_alm, device, dina         */
/*                US minutes, pressure                                     */
/*                UC tick, self_test                                       */
/*                                                                         */
/*       STATIC LOCALS: US sona_hold  - used to determine if the audible   */
/*                                      alarm should be temporarily        */
/*         (globally defined)          silenced.                           */
/*                                                                         */
/*                                                                         */
/*       AUTOMATIC LOCALS: none                                            */
/*                                                                         */
/*       ARGUMENTS: none                                                   */
/*                                                                         */
/*       CONSTANTS: AUDIO_OFF, ON, OFF, FPOUT                              */
/*                                                                         */
/*                                                                         */
/*                                                                         */
/***************************************************************************/ alm_check()

begin if (swtch.alm_reset && !old_swtch.alm_reset) then sona_hold = 0;
                                            /* temporarily silence audible */ if (*pt_alm > *pt_o_alm) then sona_hold = AUDIO_OFF+1;
                    /* enable audible if a new alarm condition occurs */

*pt_o_alm = *pt_alm;

if (*pt_alm > 0) then
        begin                           /* there is an alarm condition */
        if (++sona_hold > AUDIO_OFF) then
            bit(pt_device,HORN,ON);
          else
            bit(pt_device,HORN,OFF);
        end else
        begin                           /* no alarms so turn off sonalert */
        if (!self_test) then bit(pt_device,HORN,OFF);
        end                     /* don't turn off the self test audible */ if (!swtch.pset) then
        begin if ( (alm.pres1||alm.pres2||alm.pres3||self_test) && tick ) then
            begin
            bit(pt_device,P_RIPPLE,ON);   /* blank the pressure display */
            dis_pres(0);
            end
```

```
              else
                begin
                  bit(pt_device,P_RIPPLE,OFF);
                  dis_pres(pressure);          /* update the pressure display */
                end
          end if (!swtch.tset) then
          begin if ((alm.time || self_test) && tick) then
                begin
                  bit(pt_device,T_RIPPLE,ON);   /* blank the time display */
                  dis_time(0);
                end else
                begin
                  bit(pt_device,T_RIPPLE,OFF);
                  dis_time(minutes);            /* update time display */
                end end if (!adaptive) then                       /* flash adaptive LED if needed */
          begin
            if ((alm.dina1 || alm.dina2 || alm.dina3 || alm.dina4) && tick) then
                bit(pt_dina,ADAPTLED,ON);
              else
                bit(pt_dina,ADAPTLED,OFF);
          end out(DINALED,*pt_dina);

devout();

end

/************************************************************************/
/*    PUMP.TK    *                                                      */
/******************                                                     */
/*                                                                      */
/*    THE ROUTINE: pump()                                               */
/*    ---------                                                         */
/*    This routine operates the pump until the pressure is brought back */
/*    up to the set value. If the rate of increase is not sufficient (ie*/
/*    possibly indicating a leak or kink) or if the pressure takes too  */
/*    long to rise above 30mmHg an alarm will be activated.             */
/*                                                                      */
/*                                                                      */
/*        THIS ROUTINE CALLS: sense, kinkcheck, time, devout            */
/*                                                                      */
/*        GLOBALS: STR device, alm                                      */
/*                 US pressure, P_set                                   */
/*                 US timer1                                            */
/*                                                                      */
/*        STATIC LOCALS: none                                           */
/*                                                                      */
/*        AUTOMATIC LOCALS: US dp[4], old_ave, ave                      */
/*                          UC dp_count                                 */
/*                                                                      */
/*        ARGUMENTS: none                                               */
/*                                                                      */
/*        CONSTANTS: ON, OFF, FPOUT, LOW_TIME                           */
/*                                                                      */
/*                                                                      */
/*                                                                      */
/************************************************************************/
```

```
pump()

begin
unsigned short dp[4], old_ave, ave;
unsigned char dp_count;

ave = pressure;

bit(pt_device,PUMP,ON);
    bit(pt_device,VALVE,OFF);
    devout();

while (pressure < p_set)
        begin old_ave = ave;

for (dp_count = 0; (dp_count < 4) && (pressure < p_set); ++dp_count)
            begin
            timer1 = 0;
            while((timer1 < 25) && (pressure<p_set)) pressure = sense();
            dp[dp_count] = pressure;
            end if (pressure < p_set) then
            begin
            ave = (dp[0] + dp[1] + dp[2] + dp[3]) >> 2;

if (ave > (old_ave + 4)) then    /* both expressions must always*/
                                             /* be +ve as #'s are unsigned  */
                bit(pt_alm,PRES1,OFF);                        /* dP/dT OK */
              else
                begin                                         /* dP/dT not OK */ if (pressure >= 30) then
                    kinkcheck(); /*pressure sufficient to check for kinks */ else
                    begin
                    timer1 = 0;                  /* P is low (time limit) */ while ((pressure < 30) && (p_set >= 30))
                        begin
                        pressure = sense();
                        if (timer1 >= LOW_TIME) then
                            bit(pt_alm,PRES3,ON);
                        end bit(pt_alm,PRES3,OFF);
                    end ave = pressure;  /* ave must be re-synced to the pressure */
                end
            end
        end bit(pt_device,PUMP,OFF);    /* pressure is now OK so exit pump routine */
    devout();
end
```

```
/************************************************************************/
/*      VALVE.TK     *                                                  */
/*******************                                                    */
/*                                                                      */
/*      THE ROUTINE: valve()                                            */
/*                  ---------                                           */
/*      This routine operates the valve until the pressure is brought back */
/*      down to the set value. If the rate of decrease is not sufficient */
/*      (ie possibly indicating a kink) an alarm will be activated.     */
/*                                                                      */
/*                                                                      */
/*          THIS ROUTINE CALLS: sense, kinkcheck, v_kinkcheck, delay, devout */
/*                                                                      */
/*          GLOBALS: STR device, alm                                    */
/*                   US pressure, p_set                                 */
/*                   US timer1                                          */
/*                                                                      */
/*          STATIC LOCALS: none                                         */
/*                                                                      */
/*          AUTOMATIC LOCALS: US dp[4], old_ave, ave                    */
/*                            UC dp_count                               */
/*                                                                      */
/*          ARGUMENTS: none                                             */
/*                                                                      */
/*          CONSTANTS: ON, OFF                                          */
/*                                                                      */
/*                                                                      */
/*                                                                      */
/************************************************************************/ valve()

begin
unsigned short dp[4], old_ave, ave;
unsigned char dp_count;

ave = pressure;

bit(pt_device,PUMP,OFF);
    bit(pt_device,VALVE,ON);
    devout();

while (pressure > p_set)
        begin old_ave = ave;

for (dp_count = 0; (dp_count < 4) && (pressure > p_set); ++dp_count)
            begin
            timer1 = 0;
            while((timer1 < 25) && (pressure>p_set)) pressure = sense();
            dp[dp_count] = pressure;
            end
        if (pressure > p_set) then
            begin
            ave = (dp[0] + dp[1] + dp[2] + dp[3]) >> 2;

if (old_ave > (ave + 4)) then
                bit(pt_alm,PRES1,OFF);                          /* dP/dT OK */ else
                    begin                                       /* dP/dT not OK */
                    bit(pt_device,VALVE,OFF); /* shut valve during kinkchecks */
                    v_kinkcheck();            /* so that excessive deflation */
                    while (alm.pres2)         /* doesn't occur during delay */
                        begin                 /* periods */
                        v_kinkcheck();

if (alm.pres2) then
                            begin
                            kinkcheck();
```

```
                    while (alm.pres1)       /* loop until problem is    */
                        begin               /* removed & do not risk    */
                        delay(200);         /* deflating cuff           */
                        kinkcheck();
                        end delay(200);             /* ensure delay between checks */
                    end                     /* if pres2 but not pres1 alarm */
                end bit(pt_device,VALVE,ON);  /* reopen valve after kinkchecks */
            ave = pressure;   /* ave must be re-synced to the pressure */
            end end
    end bit(pt_device,VALVE,OFF);  /* pressure is now OK so exit valve routine */
    devout();
end
/****************************************************************/
/* KINKCK.TK    *                                                */
/****************                                                */
/*                                                               */
/* THE ROUTINE: kinkcheck()                                      */
/*              -----------                                      */
/* This routine attempts to test the integrity of the control cct by */
/* operating the pump for a short time (the actual length depends on */
/* the sensed pressure) and then verifying that an appropriate pressure*/
/* increase occured.                                             */
/*                                                               */
/*                                                               */
/*     THIS ROUTINE CALLS: delay, sense, devout                  */
/*                                                               */
/*     GLOBALS: STR device, alm                                  */
/*              US pressure, kc_on[8]                            */
/*                                                               */
/*     STATIC LOCALS: none                                       */
/*                                                               */
/*     AUTOMATIC LOCALS: US p, pmp, vlv                          */
/*                                                               */
/*     ARGUMENTS: none                                           */
/*                                                               */
/*     CONSTANTS: ON, OFF                                        */
/*                                                               */
/*                                                               */
/*                                                               */
/****************************************************************/ kinkcheck()

begin
unsigned short p, pmp, vlv;
unsigned char i;

p = pressure;

if (p >= 30) then               /* sufficient pressure to do the kinktest */
        begin pmp = device.pump;          /* restore dev's to entry state on exit */
        vlv = device.valve;
        bit(pt_device,PUMP,ON);
        bit(pt_device,VALVE,OFF);
        devout();                   /*   turn on pump for a length of time */
        delay( kc_on[p>>6] );       /* dependant on the pressure (8 ranges) */
        bit(pt_device,PUMP,OFF);
        devout();                                   /* turn pump back off again */
```

```
            for (i = 0; i <= 2; ++i)         /* 3 point average over 120 ms */
                begin
                delay(4);
                pressure = sense();
                end if (pressure > (p + 4)) then
                bit(pt_alm,PRES1,OFF);

else
                    bit(pt_alm,PRES1,ON);

bit(pt_device,PUMP,pmp);/* restore device states before exiting */
            bit(pt_device,VALVE,vlv);
            devout();

end else
            bit(pt_alm,PRES1,OFF);      /* pressure is too low to do kinktest */
end /*********************************************************************/
/*    VKNKCK.TK     *                                                 */
/***************                                                      */
/*                                                                    */
/*    THE ROUTINE: v_Kinkcheck()                                      */
/*    ----------------                                                */
/*    This routine attempts to test the integrity of the control cct by */
/*    operating the valve for a short time (the actual length depends on */
/*    the sensed pressure) and then verifying that an appropriate pressure*/
/*    decrease occured.                                               */
/*                                                                    */
/*                                                                    */
/*        THIS ROUTINE CALLS: delay, sense, devout                    */
/*                                                                    */
/*        GLOBALS: STR device, alm                                    */
/*                 US pressure, v_Kc_on[8]                            */
/*                                                                    */
/*        STATIC LOCALS: none                                         */
/*                                                                    */
/*        AUTOMATIC LOCALS: US p, pmp, vlv                            */
/*                                                                    */
/*        ARGUMENTS: none                                             */
/*                                                                    */
/*        CONSTANTS: ON, OFF                                          */
/*                                                                    */
/*                                                                    */
/*                                                                    */
/*********************************************************************/ v_Kinkcheck()

begin
unsigned short p, pmp, vlv;
unsigned char i;

p = pressure;

if (p >= 30) then         /* sufficient pressure to do the kinktest */
        begin pmp = device.pump;      /* restore dev's to entry state on exit */
        vlv = device.valve;
        bit(pt_device,PUMP,OFF);
        bit(pt_device,VALVE,ON);
        devout();                   /*  turn on valve for a length of time */
        delay( v_Kc_on[p>>6] ); /* dependant on the pressure (8 ranges) */
        bit(pt_device,VALVE,OFF);
        devout();                            /* turn valve back off again */
```

```
        for (i = 0; i <= 2; ++i)              /* 3 point average over 120 ms */
            begin
            delay(4);
            pressure = sense();
            end if ( > (pressure + 4)) then
            bit(pt_alm,PRES2,OFF);

else
               bit(pt_alm,PRES2,ON);

bit(pt_device,PUMP,pmp);/* restore device states before exiting */
            bit(pt_device,VALVE,vlv);
            devout();

end else
            bit(pt_alm,PRES2,OFF);     /* pressure is too low to do kinktest */ end
```

```
/***********************************************************************/
/*    SENSE.TK    *                                                    */
/*****************                                                     */
/*                                                                     */
/*    THE ROUTINE: sense()                                             */
/*                 ---------                                           */
/*                                                                     */
/*    This routine reads the A/D converter & multiplies by 2 to determine */
/*    the pressure. It then returns with this value averaged with the  */
/*    previous 2 readings.                                             */
/*                                                                     */
/*                                                                     */
/*        THIS ROUTINE CALLS: nothing                                  */
/*                                                                     */
/*        GLOBALS: none                                                */
/*                                                                     */
/*        STATIC LOCALS: US p1, p2, p3    (globally defined)           */
/*                                                                     */
/*        AUTOMATIC LOCALS: US i                                       */
/*                                                                     */
/*        ARGUMENTS: none                                              */
/*                                                                     */
/*        CONSTANTS: A_D                                               */
/*                                                                     */
/*                                                                     */
/*                                                                     */
/***********************************************************************/ sense()

begin
unsigned short i;

out(A_D, 0);                              /* initiate an A/D conversion */
    for (i=0; i < 5; ++i);     /* delay until A/D conversion is finished */
    p1 = p2;                   /* approximately 26us per loop            */
    p2 = p3;
    p3 = in(A_D) *2;           /* read the result of the conversion      */
    return( (p1 + p2 + p3) / 3 );
end
```

```
/********************************************************************/
/*   DIVIDE.TK    *                                                 */
/*****************                                                  */
/*                                                                  */
/*   THE ROUTINE: divide(dividend,divisor,quotient)                 */
/*                ---------------------------------                 */
/*      This integer divide routine divides the dividend by the divisor */
/*      storing the result in the location pointed to by the quotient. */
/*      The remainder is returned by the routine. he dividend and the */
/*      divisor must be such that the expected result is between 0 and */
/*      15 inclusive. THis routine is used in TK binary to decimal  */
/*      conversions in the hope that it will be faster than the general */
/*      purpose divide routine of C.                                */
/*                                                                  */
/*      THIS ROUTINE CALLS: nothing                                 */
/*                                                                  */
/*      GLOBALS: none                                               */
/*                                                                  */
/*      STATIC LOCALS: none                                         */
/*                                                                  */
/*      AUTOMATIC LOCALS: US temp                                   */
/*                        C  i                                      */
/*                                                                  */
/*      ARGUMENTS: US dividend, divisor                             */
/*                 PTR quotient                                     */
/*                                                                  */
/*      CONSTANTS: none                                             */
/*                                                                  */
/*                                                                  */
/********************************************************************/ divide(dividend,divisor,quotient)
unsigned short dividend,divisor,*quotient;

begin
   unsigned short temp;
   char i;

*quotient = 0;

for (i=3; i >= 0; --i)
       begin
       *quotient = *quotient << 1;
       temp = dividend >> i;

if (temp >= divisor) then
           begin
           ++(*quotient);
           dividend = (dividend & ~(~0<<i)) + ((temp - divisor) << i);
           end end
       return(dividend);                            /* the remainder */
end
```

```
/******************************************************************/
/*   DISPRS.TK    *                                                */
/****************                                                  */
/*                                                                 */
/*   THE ROUTINE: dis_pres(p)                                      */
/*               --------------                                    */
/*                                                                 */
/*   This routine is similar to "dis_time" except that its output goes */
/*   to the pressure display.                                      */
/*                                                                 */
/*                                                                 */
/*       THIS ROUTINE CALLS: nothing                               */
/*                                                                 */
/*       GLOBALS: none                                             */
/*                                                                 */
/*       STATIC LOCALS: none                                       */
/*                                                                 */
/*       AUTOMATIC LOCALS: US hund, ten, one                       */
/*                                                                 */
/*       ARGUMENTS: US p                                           */
/*                                                                 */
/*       CONSTANTS: DISP, DK_MODE, DK_IB, DK_WRITE                 */
/*                                                                 */
/*                                                                 */
/*                                                                 */
/******************************************************************/ dis_pres(p)
  unsigned short p;

begin
  unsigned short hund, ten, one;

out(DK_MODE,DK_IB);              /* output does not affect time displays */
    out(DK_MODE,DK_WRITE);           /* initialize display address */ one = divide( divide(p,100,&hund), 10, &ten);

if (hund == 0) then hund = 0x0F;
    if ( (hund == 0x0F) && (ten == 0) ) then ten = 0x0F;

out(DISP, hund << 4);                        /* hundreds digit */
    out(DISP, ten << 4);                         /* tens digit     */
    out(DISP, one << 4);                         /* ones digit     */
end
/******************************************************************/
/*   DISTIM.TK    *                                                */
/****************                                                  */
/*                                                                 */
/*   THE ROUTINE: dis_time(time)                                   */
/*               ----------------                                  */
/*                                                                 */
/*   This routine will output the INTEGER value "time" to the time */
/*   display of the frontpanel.                                    */
/*                                                                 */
/*   - This routine looks after all of the bit manipulations necessary */
/*     to put time into the format required by the frontpanel.     */
/*                                                                 */
/*                                                                 */
/*       THIS ROUTINE CALLS: nothing                               */
/*                                                                 */
/*       GLOBALS: none                                             */
/*                                                                 */
/*       STATIC LOCALS: US hund, ten, one                          */
/*                                                                 */
/*       AUTOMATIC LOCALS: none                                    */
/*                                                                 */
/*       ARGUMENTS: US time                                        */
/*                                                                 */
/*       CONSTANTS: DISP, DK_MODE, DK_IA, DK_WRITE                 */
/*                                                                 */
/*                                                                 */
/*                                                                 */
/******************************************************************/
```

```
dis_time(time)

unsigned short time;

begin
  unsigned short hund, ten, one;

out(DK_MODE,DK_IA);        /* output does not affect pressure displays */
    out(DK_MODE,DK_WRITE);                     /* set up display address */ one = divide( divide(time,100,&hund), 10, &ten);

if (hund == 0) then hund = 0x0F;
    if ( (hund == 0x0F) && (ten == 0) ) then ten = 0x0F;

out(DISP, hund);                              /* hundreds digit */
    out(DISP, ten);                               /* tens digit     */
    out(DISP, one);                               /* ones digit     */
end /****************************************************************************/
/*     BIT.TK     *                                                        */
/*****************                                                         */
/*                                                                         */
/*   THE ROUTINE: bit(pointer,bits,value)                                  */
/*   -----------------------                                               */
/*   This routine assigns the bit "bits" the value "value" in the          */
/*   bitfield pointed to by "pointer".                                     */
/*                                                                         */
/*   -This routine would not be necessary if the bit assignments worked    */
/*    as they should in the Whitesmith C.                                  */
/*                                                                         */
/*                                                                         */
/*       THIS ROUTINE CALLS: nothing                                       */
/*                                                                         */
/*       GLOBALS: none                                                     */
/*                                                                         */
/*       STATIC LOCALS: none                                               */
/*                                                                         */
/*       AUTOMATIC LOCALS: none                                            */
/*                                                                         */
/*       ARGUMENTS: US   *pointer, bits, value                             */
/*                                                                         */
/*       CONSTANTS: none                                                   */
/*                                                                         */
/*                                                                         */
/*                                                                         */
/****************************************************************************/ bit(pointer, bits, value)

unsigned short *pointer, bits, value;

begin if (value) then
        *pointer |= bits;

else
        *pointer &= ~bits;

end
```

```
/***********************************************************************/
/*    DEVOUT.T2K   *                                                    */
/******************                                                     */
/*                                                                      */
/*    THE ROUTINE: devout()                                             */
/*                 ---------                                            */
/*                                                                      */
/*       This routine outputs the programs device register to the device */
/*       port after complementing the data since the device drivers are  */
/*       active low on the MARK2 tourniquet.                             */
/*                                                                      */
/*       THIS ROUTINE CALLS: nothing                                    */
/*                                                                      */
/*       GLOBALS: STR device                                            */
/*                                                                      */
/*       STATIC LOCALS: none                                            */
/*                                                                      */
/*       AUTOMATIC LOCALS: none                                         */
/*                                                                      */
/*       ARGUMENTS: none                                                */
/*                                                                      */
/*       CONSTANTS: FPOUT                                               */
/*                                                                      */
/***********************************************************************/ devout()
begin out(FPOUT, ~*pt_device);

end

/***********************************************************************/
/*    DELAY.TK    *                                                     */
/******************                                                     */
/*                                                                      */
/*    THE ROUTINE: delay(how_long)                                      */
/*                 ---------------                                      */
/*                                                                      */
/*       This routine will return after delaying for "how_long" number  */
/*       of 10 milliseconds.                                            */
/*                                                                      */
/*       - as this routine uses "time", see "time" for parameter limits. */
/*                                                                      */
/*       THIS ROUTINE CALLS: time                                       */
/*                                                                      */
/*       GLOBALS: US timer2                                             */
/*                                                                      */
/*       STATIC LOCALS: none                                            */
/*                                                                      */
/*       AUTOMATIC LOCALS: none                                         */
/*                                                                      */
/*       ARGUMENTS: US how_long                                         */
/*                                                                      */
/*       CONSTANTS: none                                                */
/*                                                                      */
/*                                                                      */
/***********************************************************************/ delay(how_long)

unsigned short how_long;

begin timer2 = 0;
    while (timer2 <= how_long);
end
```

```
/*************************************************************************/
/*   SERIAL.TK    *                                                     */
/******************                                                     */
/*                                                                      */
/*   THE ROUTINE: serial()                                              */
/*                ---------                                             */
/*                                                                      */
/*      This routine checks the serial port to determine if there is a  */
/*      character ready to be read (if so it reads it and stores it in  */
/*      a buffer ready for printing). If the transmitter is ready       */
/*      to accept a character It then sends one if there are any        */
/*      waiting to be sent.                                             */
/*                                                                      */
/*      THIS ROUTINE CALLS: que, d_que, dina_store                      */
/*                                                                      */
/*      GLOBALS: US nodata     used as a timing counter to determine if */
/*                             end of string from dinamp reached        */
/*                                                                      */
/*               CHAR c_buff[5] buffer to hold last 5 chars recieved -  */
/*                              used by "adapt" to determine systolic   */
/*                                                                      */
/*                   *pointer points to next character to be printed    */
/*                                                                      */
/*                   mdl_ptr  a flag = HIGH if "pointer" is valid       */
/*                                                                      */
/*      STATIC LOCALS: none                                             */
/*                                                                      */
/*      AUTOMATIC LOCALS: US s_status     port status                   */
/*                                                                      */
/*      ARGUMENTS: none                                                 */
/*                                                                      */
/*      CONSTANTS: HIGH, LOW, BUFFER, ST_DATA, SR_DATA, S_DATA,         */
/*                 DINA_TIME                                            */
/*                                                                      */
/*                                                                      */
/*************************************************************************/ serial()
begin
   unsigned short s_status;
   unsigned char *d_que(), *dina_store();

s_status = in(S_STATUS);                     /* read serial port status */ begin                                        /* input port handling */
   if (nodata <= DINA_TIME) then ++nodata;

if (nodata == DINA_TIME) then                /* end of string reached */
      begin
      dina_store('\n');    /* linefeed takes place of reset line from */
                           /* DINAMAP to printer                       */
      dina_store('\0');                         /* end of string character */
      que(din_string);     /* place this string into the printer que */
      end if (s_status & SR_DATA) then  /* there's a character in the reciever */
   begin c_buff[4]=c_buff[3]; /* done explicitly instead of with a loop */
   c_buff[3]=c_buff[2]; /* to make execution faster               */
   c_buff[2]=c_buff[1];
   c_buff[1]=c_buff[0];
   c_buff[0]=in(S_DATA) & 0x7f;    /* mask off the high order bit */ if (nodata >= DINA_TIME) then             /* start of a new string */
      begin
      if (BUFFER - dina_ptr < (BUFFER / 5)) then dina_ptr = 0;
            /* ensure a reasonable space  before end of buffer */
      din_string = dina_store(c_buff[0]);  /*str first char & save*/
                                           /* pointer to it          */
      nodata = 0;
      end
```

```
              else
                begin
                  dina_store(c_buff[0]);         /* attach character to string */
                  nodata = 0;
                end end
        end
  begin                                           /* output port handling */
  if (s_status & ST_DATA) then                    /* transmitter ready */ if (mdl_ptr) then                           /* in the middle of a string */
          begin if (*pointer != '\0') then
              begin if ((*pointer == '\n') || (*pointer == '\015')) then
                                                  /* pad cr/lf w/ nulls so */
                  begin                           /* printer can keep up   */ if (null_cnt == 0) then out(S_DATA,'\n');
                                      else out(S_DATA,'\0'); /* null */ if (++null_cnt > NULL) then
                      begin
                      null_cnt = 0;
                      ++pointer;
                      end
                  end else out(S_DATA,*pointer++);
                  end else mdl_ptr = LOW;
              end else
              if (que_ptr != d_que_ptr) then      /* pointer que not empty */
                  begin
                  pointer = d_que();
                  mdl_ptr = HIGH;
                  end
      end
  end
/****************************************************************************/
/*      TRAP.TK        #                                                    */
/***************                                                            */
/*                                                                          */
/*      THE ROUTINE: trap()                                                 */
/*      --------                                                            */
/*      This is a null routine. The hardware trap is not used in this       */
/*      implementation.                                                     */
/*                                                                          */
/*                                                                          */
/*      THIS ROUTINE CALLS: nothing                                         */
/*                                                                          */
/*      GLOBALS: none                                                       */
/*                                                                          */
/*      STATIC LOCALS: none                                                 */
/*                                                                          */
/*      AUTOMATIC LOCALS: none                                              */
/*                                                                          */
/*      ARGUMENTS: none                                                     */
/*                                                                          */
/*      CONSTANTS: none                                                     */
/*                                                                          */
/*                                                                          */
/*                                                                          */
/****************************************************************************/
trap()
begin
end
```

```
/****************************************************************************/
/* DINSTR.AT2  *                                                            */
/***************                                                            */
/*                                                                          */
/*    THE ROUTINE: dina_store(charac)                                       */
/*                 ------------------                                       */
/*                                                                          */
/*       This routine places "charac" in a buffer "dina_buff[BUFFER+1]"     */
/*       which is mean't to hold strings received from the dinamap.         */
/*       If the end of the buffer is reached the present string is          */
/*       terminated and a new one is started at the beginning of the        */
/*       buffer.                                                            */
/*                                                                          */
/*       the routine which calls this routine should execute the            */
/*       following statement before starting a new string to ensure that    */
/*       there will probably be sufficient space in the buffer to hold      */
/*       the string contiguously:                                           */
/*         if ((BUFFER - dina_ptr) < (BUFFER / 5)) then dina_ptr = 0;       */
/*                                                                          */
/*       THIS ROUTINE CALLS: nothing                                        */
/*                                                                          */
/*       GLOBALS: char dina_buff[BUFFER+1]   the string buffer              */
/*                     *din_string           points to beginning of         */
/*                                           current string                 */
/*                US   dina_ptr              the next location in           */
/*                                           dina_buff to store charac      */
/*                                                                          */
/*       STATIC LOCALS: none                                                */
/*                                                                          */
/*       AUTOMATIC LOCALS: temp                                             */
/*                                                                          */
/*       ARGUMENTS: charac                                                  */
/*                                                                          */
/*       CONSTANTS: BUFFER  the length-1 of the string buffer               */
/*                                                                          */
/*                                                                          */
/****************************************************************************/ unsigned char *dina_store(charac)
unsigned short charac;

begin
   unsigned char *temp;

dina_buff[dina_ptr] = charac;
      temp = &dina_buff[dina_ptr];

if (++dina_ptr >= BUFFER) then/* reached end of buffer, end string  */
           begin                    /* & start new string at beginning of */
           dina_buff[BUFFER] = dina_buff[0] = '\0';  /* buffer            */
           dina_ptr = 0;
           que(din_string);
           din_string = &dina_buff[0];
           end return(temp);
end
```

```
/***********************************************************************/
/*  TKSTR.AT2    *                                                      */
/*****************                                                      */
/*                                                                      */
/*   THE ROUTINE: tk_store(charac)                                      */
/*                ---------------                                       */
/*                                                                      */
/*      This routine places "charac" in a buffer "tk_buff[TK_BUFFER+1]" */
/*      which is mean't to hold numerical strings which must be         */
/*      assembled by the tourniquet. ie variable quantities such as     */
/*      the time and pressure.                                          */
/*                                                                      */
/*      If the end of the buffer is reached the present string is       */
/*      terminated and a new one is started at the beginning of the     */
/*      buffer.                                                         */
/*                                                                      */
/*      The routine which calls this routine should execute the         */
/*      following statement before starting a new string to ensure that */
/*      there will probably be sufficient space in the buffer to hold   */
/*      the string contiguously:                                        */
/*         if ((TK_BUFFER - tk_ptr) < (TK_BUFFER / 5)) then tk_ptr = 0;  */
/*                                                                      */
/*      This routine operates in the same manner as "dina_store".       */
/*      a separate routine is needed though as the characters from the  */
/*      dinamap come in quite slowly (30/s), and TK messages must not   */
/*      mixed in the middle of these.                                   */
/*                                                                      */
/*      THIS ROUTINE CALLS: nothing                                     */
/*                                                                      */
/*      GLOBALS: char tk_buff[TK_BUFFER+1]   the string buffer          */
/*                    *tk_string             points to beginning of     */
/*                                           current string             */
/*               US   tk_ptr                 the next location in       */
/*                                           tk_buff to store charac    */
/*                                                                      */
/*      STATIC LOCALS: none                                             */
/*                                                                      */
/*      AUTOMATIC LOCALS: temp                                          */
/*                                                                      */
/*      ARGUMENTS: charac                                               */
/*                                                                      */
/*      CONSTANTS: TK_BUFFER  the length-1 of the string buffer         */
/*                                                                      */
/***********************************************************************/ unsigned char *tk_store(charac)
unsigned short charac;

begin
   unsigned char *temp;

tk_buff[tk_ptr] = charac;
      temp = &tk_buff[tk_ptr];

if (++tk_ptr >= TK_BUFFER) then/* reached end of buffer, end string */
         begin                    /* & start new string at beginning of */
         tk_buff[TK_BUFFER] = tk_buff[0] = '\0';    /* buffer            */
         tk_ptr = 0;
         que(tk_string);
         tk_string = &tk_buff[0];
         end return(temp);
end
```

```
/******************************************************************/
/* NUMSTR.AT2    *                                                */
/****************                                                 */
/*                                                                */
/*   THE ROUTINE: num_store(number)                               */
/*                -------------------                             */
/*                                                                */
/*      This routine outputs the unsigned three digit integer "number" */
/*      to the printer. That is it breaks "number" up into digits, */
/*      assembles a string out of these using "tk_store", and then */
/*      "ques" a pointer to this string.                          */
/*                                                                */
/*      THIS ROUTINE CALLS: tk_store, divide, que                 */
/*                                                                */
/*      GLOBALS: tk_ptr                                           */
/*                                                                */
/*      STATIC LOCALS: none                                       */
/*                                                                */
/*      AUTOMATIC LOCALS: US hund, ten, one                       */
/*                                                                */
/*      ARGUMENTS: number                                         */
/*                                                                */
/*      CONSTANTS: TK_BUFFER                                      */
/*                                                                */
/*                                                                */
/******************************************************************/ num_store(number)
unsigned short number;

begin
   unsigned short hund, ten, one;
   unsigned char *tk_store();

if ((TK_BUFFER - tk_ptr) < (TK_BUFFER / 5)) then tk_ptr = 0;
   /* ensure that there is room in buffer to store string contiguously */ tk_string = tk_store(' ');              /* precede number w/ a space */ one = divide( divide(number,100,&hund), 10, &ten);

if (hund != 0) then tk_store(hund + '0');
   if ((hund != 0) | (ten != 0)) then tk_store(ten + '0');
   tk_store(one + '0');

tk_store('\0');                         /* end of string character */ que(tk_string);
   end
```

```
/***********************************************************************/
/*    QUE.AT2       *                                                   */
/******************                                                     */
/*                                                                      */
/*    THE ROUTINE: que(pointer)                                         */
/*                 ------------                                         */
/*                                                                      */
/*        This routine places "pointer" in a que of pointers to strings */
/*        of text (the text strings are terminated by a '\0'). The      */
/*        pointer que is "Q_BUFFER elements long.                       */
/*                                                                      */
/*        THIS ROUTINE CALLS: nothing                                   */
/*                                                                      */
/*        GLOBALS: char que_buff[Q_BUFFER]   the pointer que            */
/*                 US que_ptr, d_que_ptr     pointers to the next       */
/*                                           locations from which to put*/
/*                                           and get a string pointer   */
/*                                                                      */
/*        STATIC LOCALS: none                                           */
/*                                                                      */
/*        AUTOMATIC LOCALS: none                                        */
/*                                                                      */
/*        ARGUMENTS: pointer                                            */
/*                                                                      */
/*        CONSTANTS: Q_BUFFER                                           */
/*                                                                      */
/*                                                                      */
/***********************************************************************/ que(pointer)
char *pointer;

begin
    que_buff[que_ptr++] = pointer;
    if (que_ptr >= Q_BUFFER) then que_ptr = 0;
end
/***********************************************************************/
/*    DQUE.AT2      *                                                   */
/******************                                                     */
/*                                                                      */
/*    THE ROUTINE: d_que()                                              */
/*                 --------                                             */
/*                                                                      */
/*        This routine returns the next pointer to a text string from a */
/*        que of pointers which is "Q_BUFFER" elements long.            */
/*                                                                      */
/*        THIS ROUTINE CALLS: nothing                                   */
/*                                                                      */
/*        GLOBALS: char que_buff[Q_BUFFER]   the pointer que            */
/*                 US que_ptr, d_que_ptr     pointers to the next       */
/*                                           locations from which to put*/
/*                                           and get a string pointer   */
/*                                                                      */
/*        STATIC LOCALS: none                                           */
/*                                                                      */
/*        AUTOMATIC LOCALS: none                                        */
/*                                                                      */
/*        ARGUMENTS: none                                               */
/*                                                                      */
/*        CONSTANTS: Q_BUFFER                                           */
/*                                                                      */
/*                                                                      */
/***********************************************************************/ unsigned char *d_que()
    begin
      unsigned char *temp;
        temp = que_buff[d_que_ptr++];
        if (d_que_ptr >= Q_BUFFER) then d_que_ptr = 0;
        return(temp);
    end
```

```
/***********************************************************************/
/*  PRTMSG.AT2  *                                                      */
/****************                                                      */
/*                                                                     */
/*   THE ROUTINE: print_msg()                                          */
/*               ------------                                          */
/*                                                                     */
/*      This routine is called every TIME2 10msec to que any messages  */
/*      as required by the tourniquet. These messages may be the result*/
/*      of switch activations or alarm conditions.                     */
/*                                                                     */
/*      THIS ROUTINE CALLS: numstr, que, elapse                        */
/*                                                                     */
/*      GLOBALS: CHAR *msg1 - *msg30                                   */
/*               US p_set, old_pset, t_set, old_tset                   */
/*      (logical) CHAR adapt, old_adapt                                */
/*                PTR swtch, old_swtch, alm, old_alm                   */
/*                                                                     */
/*      STATIC LOCALS: none                                            */
/*                                                                     */
/*      AUTOMATIC LOCALS: none                                         */
/*                                                                     */
/*      ARGUMENTS: none                                                */
/*                                                                     */
/*      CONSTANTS: none                                                */
/*                                                                     */
/*                                                                     */
/***********************************************************************/ print_msg()

begin if (swtch.alm_reset && !old_swtch.alm_reset) then /* functional msgs*/
        begin
        que(msg13);
        que(msg1);
        elapse();
        que(msg12);
        end if (swtch.infl_strt && !old_swtch.infl_strt) then
        begin
        que(msg13);
        que(msg2);
        que(msg6);
        num_store(p_set);
        que(msg5);
        elapse();
        que(msg12);
        end if (old_adaptive != adaptive) then
        begin
        que(msg13);
        que(msg28);
        if (adaptive) then que(msg7);
                      else que(msg8);
        elapse();
        que(msg12);
        old_adaptive = adaptive;
        end
```

```
if (old_pset != p_set) then
    begin
    que(msg13);
    que(msg10);
    num_store(old_pset);
    que(msg11);
    num_store(p_set);
    que(msg5);
    elapse();
    que(msg12);
    old_pset = p_set;
    end if (old_tset != t_set) then
    begin
    que(msg13);
    que(msg9);
    num_store(old_tset);
    que(msg11);
    num_store(t_set);
    que(msg4);
    elapse();
    que(msg12);
    old_tset = t_set;
    end if (alm.pres1 && !dina_alm.pres1) then    /* alarm messages */
    begin
    que(msg13);
    que(msg29);
    que(msg30);
    que(msg14);
    que(msg16);
    elapse();
    que(msg12);
    end if (alm.pres2 && !dina_alm.pres2) then
    begin
    que(msg13);
    que(msg29);
    que("\n");
    que(msg14);
    que(msg17);
    elapse();
    que(msg12);
    end if (alm.pres3 && !dina_alm.pres3) then
    begin
    que(msg13);
    que(msg18);
    num_store(P_MIN);
    que(msg5);
    que(msg19);
    elapse();
    que(msg12);
    end if (alm.time && !dina_alm.time) then
    begin
    que(msg13);
    que(msg20);
    elapse();
    que(msg12);
    end
```

```
if (alm.powerfail && !dina_alm.powerfail) then
    begin
    que(msg13);
    que(msg21);
    elapse();
    que(msg12);
    end if (dina_alm.powerfail && !alm.powerfail) then
    begin
    que(msg13);
    que(msg23);
    elapse();
    que(msg12);
    end if (alm.low_batt && !dina_alm.low_batt) then
    begin
    que(msg13);
    que(msg22);
    elapse();
    que(msg12);
    end if (alm.dina1 && !dina_alm.dina1) then
    begin
    que(msg13);
    que(msg24);
    num_store(DIN_MIN);
    que(msg11);
    num_store(DIN_MAX);
    que(msg5);
    elapse();
    que(msg12);
    end if (alm.dina2 && !dina_alm.dina2) then
    begin
    que(msg13);
    que(msg25);
    elapse();
    que(msg12);
    end if (alm.dina3 && !dina_alm.dina3) then
    begin
    que(msg13);
    que(msg26);
    elapse();
    que(msg12);
    end if (alm.dina4 && !dina_alm.dina4) then
    begin
    que(msg13);
    que(msg27);
    num_store(DIN_DIF);
    que(msg5);
    elapse();
    que(msg12);
    end

*pt_d_alm = *pt_alm;    /* save old alarm status */ end
```

```
/*********************************************************************/
/*   ELAPSE.AT2   *                                                  */
/*****************                                                   */
/*                                                                   */
/*   THE ROUTINE: elapse()                                           */
/*              ----------                                           */
/*                                                                   */
/*      This routine ques ">> elapsed time = xxx minutes{CR/LF}"     */
/*      where xxx is the number of minutes since INFLATION START was */
/*      pressed.                                                     */
/*                                                                   */
/*      THIS ROUTINE CALLS: que, numstr                              */
/*                                                                   */
/*      GLOBALS: CHAR *msg3, *msg4                                   */
/*                                                                   */
/*      STATIC LOCALS: none                                          */
/*                                                                   */
/*      AUTOMATIC LOCALS: none                                       */
/*                                                                   */
/*      ARGUMENTS: none                                              */
/*                                                                   */
/*      CONSTANTS: none                                              */
/*                                                                   */
/*                                                                   */
/*********************************************************************/ elapse()

begin
    que(msg3);
    num_store(minutes);
    que(msg4);
end
```

```
/*******************************************************************/
/*   ADAPTI.AT2    *                                               */
/*****************                                                 */
/*                                                                 */
/*   THE ROUTINE: adapti()                                         */
/*   ----------                                                    */
/*                                                                 */
/*      This routine changes the mode of the TK between constant and */
/*      adaptive depending on the status of the adaptive/constant  */
/*      switch. It also checks the data coming from the dinamap for */
/*      systolic pressures and sets the appropriate adaptive alarm if */
/*      necessary. If an adaptive alarm condition exists the mode  */
/*      automatically switches back to constant and the adaptive LED */
/*      flashes. (The action of flashing the LED is actually done by */
/*      alm_check().) Depressing ALARM RESET resets any adaptive alarms.*/
/*                                                                 */
/*      Adaptive alarms:                                           */
/*          dina1: sys pres from dinamap not within acceptable limits */
/*          dina2: too long since last valid sys pres from dinamap */
/*          dina3: DINAMAP in Kpascals mode instead of mmHg        */
/*          dina4: difference in successive pres.'s from dina too great */
/*                                                                 */
/*      The pressure used for cuff inflation is a 3 pt moving average */
/*      of valid sys pressure's from the dinamap plus a safety margin. */
/*      Initially after activation of the adaptive mode all 3 pts of */
/*      the average will be set to the first valid pressure input. */
/*                                                                 */
/*      THIS ROUTINE CALLS: nothing                                */
/*                                                                 */
/*      GLOBALS: S p_adapt, rd_minute                              */
/*               STR alm, dina, swtch, old_swtch, din_marg         */
/*                                                                 */
/*      STATIC LOCALS: none                                        */
/*                                                                 */
/*      AUTOMATIC LOCALS: S diff, t1, i, old_p_adapt               */
/*                                                                 */
/*      ARGUMENTS: none                                            */
/*                                                                 */
/*      CONSTANTS: DIN_MAX, DIN_MIN, DIN_TIME, DIN_DIFF,           */
/*                 ON, OFF                                         */
/*                                                                 */
/*                                                                 */
/*******************************************************************/ adapti()
begin
   short diff,t1,i,old_p_adapt;
   unsigned char temp;

if (adaptive) then
       begin
       temp = !(c_buff[3]=='0' && c_buff[2]=='0' && c_buff[1]=='0');
           /* don't detect dinamap sys pressure of 000 as being valid */
   if (temp && !(c_buff[2]=='.') && (c_buff[0]=='/')) then
       begin                              /* valid pressure reading */ c_buff[0] = '@';    /* prevent detecting same reading twice */
       rd_minute = minutes; /* reset time since last valid p input */
       old_p_adapt = p_adapt;
       p_adapt = 0;

for (i=3; i>0; --i)                /* convert chars to binary */
           begin
           t1 = p_adapt = p_adapt << 1;
           p_adapt = p_adapt << 2;
           p_adapt += (t1 + c_buff[i] - '0');
           end
```

```
    if (strt_adapt) then
        begin
        old_p_adapt = p_adapt;
        p_ad[0] = p_ad[1] = p_ad[2] = p_adapt;
        strt_adapt = NO;
        end if ((p_adapt > DIN_MAX) || (p_adapt < DIN_MIN)) then
        bit(pt_alm,DINA1,ON);

diff = old_p_adapt - p_adapt;
    if (diff < 0) then diff = -diff;

if (diff > DIN_DIF) then bit(pt_alm,DINA4,ON);

if ( !(alm.dina1 || alm.dina4)) then  /* set new cuff press  */
        begin
        p_ad[2] = p_ad[1];
        p_ad[1] = p_ad[0];
        p_ad[0] = p_adapt;
        p_set = (p_ad[0] + p_ad[1] + p_ad[2]) /3 + din_marg;
        end end else
    begin if ((minutes - rd_minutes) >= DIN_TIME) then bit(pt_alm,DINA2,ON);

if ((c_buff[2]=='.') && (c_buff[0]=='/')) then
        bit(pt_alm,DINA3,ON);

end if (alm.dina1 || alm.dina2 || alm.dina3 || alm.dina4) then
    begin                                 /* switch out of adaptive */
    adaptive = OFF;
         p_set = p_settings;
         bit(pt_dina,CONSTLED,ON); /* almck will turn off ADAPTLED */
         end end if (swtch.alm_reset && !old_swtch.alm_reset) then /* reset any    */
        bit(pt_alm,DINA1|DINA2|DINA3|DINA4,OFF);      /* adapt alarms */ temp = !(alm.dina1 || alm.dina2 || alm.dina3 || alm.dina4);
    if (temp && swtch.adapt && !old_swtch.adapt && !adaptive) then
        begin
        adaptive = ON;
        bit(pt_dina,ADAPTLED,ON);   /* almck does output inst. to port */
        bit(pt_dina,CONSTLED,OFF);
        strt_adapt = YES;
        rd_minute = minutes;
        end if (swtch.const && !old_swtch.const) then
        begin
        adaptive = OFF;
        bit(pt_dina,CONSTLED,ON);          /* almck turns off ADAPTLED */
        p_set = p_settings;
        end end
```

I claim:

1. A pneumatic tourniquet for employing the minimum safe pressure to occlude blood flow into a patient's limb, comprising:
an inflatable cuff;
pressurizing means for pressurizing said cuff;
pressure relief means for depressurizing said cuff;
cuff pressure sensing means for sensing said cuff pressure;
blood pressure sensing means for sensing the patient's systolic blood pressure; and
pressure regulator means responsive to variations in said systolic blood pressure for selectably activating said pressurizing means and said pressure relief means to maintain the cuff pressure above said systolic blood pressure and to maintain a substantially constant pressure difference between said cuff pressure and said systolic blood pressure.

2. A pneumatic tourniquet as defined in claim 1, wherein said cuff pressure sensing means produces a cuff pressure output signal representative of said cuff pressure, said blood pressure sensing means produces a blood pressure output signal representative of said systolic blood pressure, and said pressure regulator means comprises electronic sensing and control apparatus for:
comparing said blood pressure and cuff pressure output signals;
producing a pressure decrease output signal for actuating said pressure relief means to depressurize said cuff if said cuff pressure exceeds an upper pressure limit; and
producing a pressure increase output signal for actuating said pressurizing means to pressurize said cuff if said cuff pressure is below a lower pressure limit.

3. A pneumatic tourniquet as defined in claim 2, further comprising limb indicator means for indicating whether said cuff is to occlude blood flow into an arm or into a leg of said patient.

4. A pneumatic tourniquet as defined in claim 3, wherein said upper and lower pressure limits are selected by operation of said limb indicator means.

5. A pneumatic tourniquet as defined in claim 3, wherein said limb indicator means includes a coupler for coupling between said cuff and said electronic sensing and control apparatus, said coupler having a characteristic detectable by said electronic sensing and control apparatus, which characteristic indicates whether said cuff is to occlude blood flow into an arm or into a leg of said patient.

6. A pneumatic tourniquet as defined in claim 2 wherein said electronic sensing and control apparatus further includes means for selecting a time period during which said cuff is to remain pressurized and further comprises time alarm means for producing a time alarm signal when said cuff has remained pressurized for, or in excess of, said selected time period.

7. A pneumatic tourniquet as defined in claim 1, further comprising blood pressure alarm means for producing a blood pressure alarm signal when said systolic blood pressure is less than about 80 mmHg or greater than about 160 mmHg.

8. A pneumatic tourniquet as defined in claim 7, wherein, said cuff pressure sensing means produces a cuff pressure output signal representative of said cuff pressure and said blood pressure sensing means produces a blood pressure output signal representative of said systolic blood pressure, and upon production of said blood pressure alarm signal, said pressure regulator means is rendered:
non-responsive to said blood pressure output signal; and
responsive to said cuff pressure output signal; thereby selectably activating said pressurizing means and said pressure relief means to maintain said cuff pressure near a selected pressure.

9. A pneumatic tourniquet as defined in claim 1, further comprising inhibit alarm means for producing an inhibit alarm signal when said blood pressure sensing means is unable to successively sense said systolic blood pressure for more than about 3 minutes.

10. A pneumatic tourniquet as defined in claim 9, wherein, said cuff pressure sensing means produces a cuff pressure output signal representative of said cuff pressure and said blood pressure sensing means produces a blood pressure output signal representative of said systolic blood pressure, and upon production of said inhibit alarm signal, said pressure regulator means is rendered:
non-responsive to said blood pressure output signal; and
responsive to said cuff pressure output signal; thereby selectably activating said pressurizing means and said pressure relief means to maintain said cuff pressure near a selected pressure.

11. A pneumatic tourniquet as defined in claim 1, wherein said blood pressure sensing means senses said systolic blood pressure at periodic time intervals, and further comprising blood pressure fluctuation alarm means for producing a blood pressure fluctuation alarm signal when the systolic blood pressure sensed during a particular time interval differs, by more than a selected amount, from the systolic blood pressure sensed during the immediately preceding time interval.

12. A pneumatic tourniquet as defined in claim 11, wherein, upon production of said blood pressure fluctuation alarm signal, said pressure regulator means is rendered:
non-responsive to said blood pressure output signal; and
responsive to said cuff pressure output signal;
thereby selectably activating said pressurizing means and said pressure relief means to maintain said cuff pressure near a selected pressure.

13. A pneumatic tourniquet as defined in claim 1, wherein said cuff includes:
a tourniquet cuff segment for occluding blood flow into the patient's limb; and
a blood pressure cuff segment for coupling to said blood pressure sensing means for sensing the patient's systolic blood pressure.

14. A pneumatic tourniquet as defined in claim 1, further comprising cuff pressure alarm means for producing a cuff pressure alarm signal if activation of said pressurizing means for a selected time period does not increase said cuff pressure to a value within predetermined cuff pressure limits.

15. A pneumatic tourniquet as defined in claim 1, further comprising cuff pressure alarm means for producing a cuff pressure alarm signal if activation of said pressure relief means for a selected time period does not decrease said cuff pressure to a value within pre-determined cuff pressure limits.

16. A pneumatic tourniquet as defined in claim 1, further comprising power alarm means for producing a power alarm signal upon interruption of external power supplied to said pressurizing means, said pressure relief means, said cuff pressure sensing means, or said pressure regulator means.

17. A pneumatic tourniquet as defined in claim 1, further comprising recorder means for periodically recording the operational status of said pneumatic tourniquet.

* * * * *